(12) United States Patent
Burdette et al.

(10) Patent No.: US 7,201,715 B2
(45) Date of Patent: Apr. 10, 2007

(54) REAL TIME BRACHYTHERAPY SPATIAL REGISTRATION AND VISUALIZATION SYSTEM

(75) Inventors: Everette C. Burdette, Champaign, IL (US); Bruce M. Komandina, Urbana, IL (US)

(73) Assignee: Computerized Medical Systems, Inc., St. Louis, MO (US)

(*) Notice: Subject to any disclaimer, the term of this patent is extended or adjusted under 35 U.S.C. 154(b) by 0 days.

(21) Appl. No.: 10/329,281

(22) Filed: Dec. 23, 2002

(65) Prior Publication Data

US 2003/0229282 A1    Dec. 11, 2003

Related U.S. Application Data

(63) Continuation of application No. 09/573,415, filed on May 18, 2000, now Pat. No. 6,512,942, which is a continuation of application No. 09/087,453, filed on May 29, 1998, now Pat. No. 6,129,670, which is a continuation-in-part of application No. 08/977,362, filed on Nov. 24, 1997, now Pat. No. 6,256,529.

(51) Int. Cl.
*A61N 5/00* (2006.01)

(52) U.S. Cl. .................. 600/3; 600/7; 600/8
(58) Field of Classification Search ................ 600/427, 600/439, 3, 7, 8, 1
See application file for complete search history.

(56) References Cited

U.S. PATENT DOCUMENTS

| | | | |
|---|---|---|---|
| 4,125,858 A | 11/1978 | Hounsfield et al. |
| 4,567,896 A | 2/1986 | Barnea et al. |
| 4,586,512 A | 5/1986 | Do-huu et al. |
| 4,751,643 A | 6/1988 | Lorensen et al. |
| 4,764,971 A | 8/1988 | Sullivan |
| 4,791,567 A | 12/1988 | Cline et al. |
| 4,856,074 A | 8/1989 | Nagaoka |
| 4,896,673 A | 1/1990 | Rose et al. |
| 4,961,425 A | 10/1990 | Kennedy et al. |
| 4,991,579 A | 2/1991 | Allen |
| 4,994,013 A | 2/1991 | Suthanthiran et al. |
| 5,072,384 A | 12/1991 | Doi et al. |
| 5,133,020 A | 7/1992 | Giger et al. |

(Continued)

FOREIGN PATENT DOCUMENTS

DE    198 25 999    12/1999

(Continued)

OTHER PUBLICATIONS

Holupka et al.; "Ultrasound Image Fusion For External Beam Radiotherapy For Prostate Cancer"; Int. J. Radiation Oncology Biol. Phys.; 1996; pp. 975-984; vol. 35, No. 5; Elsevier Science Inc.; USA.

(Continued)

*Primary Examiner*—Ruth S. Smith
(74) *Attorney, Agent, or Firm*—Thompson Coburn, LLP

(57) ABSTRACT

A method and system for monitoring loading of radiation into an insertion device for use in a radiation therapy treatment to determine whether the treatment will be in agreement with a radiation therapy plan. In a preferred embodiment, optical sensors and radiation sensors are used to monitor loading of radioactive seeds and spacers into a needle as part of a prostate brachytherapy treatment.

33 Claims, 27 Drawing Sheets

U.S. PATENT DOCUMENTS

| | | |
|---|---|---|
| 5,166,876 A | 11/1992 | Cline et al. |
| 5,170,790 A | 12/1992 | Lacoste et al. |
| 5,178,148 A | 1/1993 | Lacoste et al. |
| 5,185,809 A | 2/1993 | Kennedy et al. |
| 5,187,658 A | 2/1993 | Cline et al. |
| 5,204,625 A | 4/1993 | Cline et al. |
| 5,222,499 A | 6/1993 | Allen et al. |
| 5,227,969 A | 7/1993 | Waggener et al. |
| 5,234,004 A | 8/1993 | Hascoet et al. |
| 5,239,591 A | 8/1993 | Ranganath |
| 5,242,373 A | 9/1993 | Scott et al. |
| 5,260,871 A | 11/1993 | Goldberg |
| 5,289,374 A | 2/1994 | Doi et al. |
| 5,299,253 A | 3/1994 | Wessels |
| 5,319,549 A | 6/1994 | Katsuragawa et al. |
| 5,319,551 A | 6/1994 | Sekiguchi et al. |
| 5,339,812 A | 8/1994 | Hardy et al. |
| 5,371,810 A | 12/1994 | Vaidyanathan |
| 5,389,101 A | 2/1995 | Heilbrun et al. |
| 5,391,139 A | 2/1995 | Edmundson |
| 5,391,199 A | 2/1995 | Ben-Haim |
| 5,394,457 A | 2/1995 | Leibinger et al. |
| 5,398,690 A | 3/1995 | Batten et al. |
| 5,409,006 A | 4/1995 | Buchholtz et al. |
| 5,410,617 A | 4/1995 | Kidd et al. |
| 5,411,026 A | 5/1995 | Carol |
| 5,412,563 A | 5/1995 | Cline et al. |
| 5,433,199 A | 7/1995 | Cline et al. |
| 5,447,154 A | 9/1995 | Cinquin et al. |
| 5,452,367 A | 9/1995 | Bick et al. |
| 5,457,754 A | 10/1995 | Han et al. |
| 5,458,126 A | 10/1995 | Cline et al. |
| 5,460,592 A | 10/1995 | Langton et al. |
| 5,491,627 A | 2/1996 | Zhang et al. |
| 5,494,039 A | 2/1996 | Onik et al. |
| 5,517,602 A | 5/1996 | Natarajan |
| 5,526,812 A | 6/1996 | Dumoulin et al. |
| 5,531,223 A | 7/1996 | Hatanaka |
| 5,531,227 A | 7/1996 | Schneider |
| 5,537,485 A | 7/1996 | Nishikawa et al. |
| 5,553,207 A | 9/1996 | Sekiguchi et al. |
| 5,562,095 A | 10/1996 | Downey et al. |
| 5,566,246 A | 10/1996 | Rao |
| 5,570,430 A | 10/1996 | Sheehan et al. |
| 5,574,799 A | 11/1996 | Bankman et al. |
| 5,583,659 A | 12/1996 | Lee et al. |
| 5,590,215 A | 12/1996 | Allen |
| 5,603,318 A | 2/1997 | Heilbrun et al. |
| 5,622,170 A | 4/1997 | Schulz |
| 5,624,382 A | 4/1997 | Oppelt et al. |
| 5,638,819 A | 6/1997 | Manwaring et al. |
| 5,640,496 A | 6/1997 | Hardy et al. |
| 5,660,185 A | 8/1997 | Shmulewitz et al. |
| 5,662,111 A | 9/1997 | Cosman |
| 5,669,382 A | 9/1997 | Curwen et al. |
| 5,672,172 A | 9/1997 | Zupkas |
| 5,682,886 A | 11/1997 | Delp et al. |
| 5,709,206 A | 1/1998 | Teboul |
| 5,715,836 A | 2/1998 | Kliegis et al. |
| 5,727,538 A * | 3/1998 | Ellis ........................... 124/77 |
| 5,734,739 A | 3/1998 | Sheehan et al. |
| 5,740,225 A | 4/1998 | Nabatame |
| 5,742,263 A | 4/1998 | Wang et al. |
| 5,749,362 A | 5/1998 | Funda et al. |
| 5,765,561 A | 6/1998 | Chen et al. |
| 5,769,074 A | 6/1998 | Barnhill et al. |
| 5,776,063 A | 7/1998 | Dittrich et al. |
| 5,778,043 A | 7/1998 | Cosman |
| 5,787,886 A | 8/1998 | Kelly et al. |
| 5,797,849 A | 8/1998 | Vesely et al. |
| 5,810,007 A | 9/1998 | Holupka et al. |
| 5,817,022 A | 10/1998 | Vesely |
| 5,830,145 A | 11/1998 | Tenhoff |
| 5,833,627 A | 11/1998 | Shmulewitz et al. |
| 5,836,954 A | 11/1998 | Heilbrun et al. |
| 5,851,183 A | 12/1998 | Bucholz |
| 5,859,891 A | 1/1999 | Hibbard |
| 5,860,909 A | 1/1999 | Mick et al. |
| 5,868,673 A | 2/1999 | Vesely |
| 5,868,757 A | 2/1999 | Koutrouvelis |
| 5,871,448 A | 2/1999 | Ellard |
| 5,891,034 A | 4/1999 | Bucholz |
| 5,906,574 A | 5/1999 | Kan |
| 5,928,130 A | 7/1999 | Schmidt |
| 5,931,786 A | 8/1999 | Whitmore, III et al. |
| 5,938,583 A | 8/1999 | Grimm |
| 5,951,571 A | 9/1999 | Audette |
| 5,961,527 A | 10/1999 | Whitmore, III et al. |
| 5,974,165 A | 10/1999 | Giger et al. |
| 5,984,870 A | 11/1999 | Giger et al. |
| 5,989,811 A | 11/1999 | Veltri et al. |
| 6,004,267 A | 12/1999 | Tewari et al. |
| 6,006,126 A | 12/1999 | Cosman |
| 6,007,474 A | 12/1999 | Rydell |
| 6,025,128 A | 2/2000 | Veltri et al. |
| 6,027,446 A | 2/2000 | Pathak et al. |
| 6,033,357 A | 3/2000 | Ciezki et al. |
| 6,036,632 A | 3/2000 | Whitmore, III et al. |
| 6,038,467 A | 3/2000 | De Bliek et al. |
| 6,048,312 A | 4/2000 | Ishrak et al. |
| 6,083,166 A | 7/2000 | Holdaway et al. |
| 6,083,167 A | 7/2000 | Fox et al. |
| 6,095,975 A | 8/2000 | Silvern |
| 6,102,844 A | 8/2000 | Ravins et al. |
| 6,102,867 A | 8/2000 | Dietz et al. |
| 6,129,670 A * | 10/2000 | Burdette et al. ............. 600/427 |
| 6,140,065 A | 10/2000 | Carlson et al. |
| 6,146,390 A | 11/2000 | Heilbrun et al. |
| 6,165,181 A | 12/2000 | Heilbrun et al. |
| 6,167,296 A | 12/2000 | Shahidi |
| 6,179,768 B1 | 1/2001 | Loffler et al. |
| 6,196,963 B1 | 3/2001 | Williams |
| 6,196,964 B1 | 3/2001 | Loffler et al. |
| 6,206,832 B1 | 3/2001 | Downey et al. |
| 6,208,883 B1 | 3/2001 | Holupka et al. |
| 6,210,315 B1 | 4/2001 | Andrews et al. |
| 6,213,110 B1 * | 4/2001 | Christopher et al. ........ 124/51.1 |
| 6,213,932 B1 | 4/2001 | Schmidt |
| 6,236,875 B1 | 5/2001 | Bucholz et al. |
| 6,238,342 B1 | 5/2001 | Feleppa et al. |
| 6,241,670 B1 | 6/2001 | Nambu |
| 6,249,594 B1 | 6/2001 | Hibbard |
| 6,256,529 B1 | 7/2001 | Holupka et al. |
| 6,261,219 B1 * | 7/2001 | Meloul et al. ................... 600/3 |
| 6,266,453 B1 | 7/2001 | Hibbard et al. |
| 6,270,472 B1 | 8/2001 | Antaki et al. |
| 6,301,495 B1 | 10/2001 | Gueziec et al. |
| 6,311,084 B1 | 10/2001 | Cormack et al. |
| 6,325,758 B1 | 12/2001 | Carol et al. |
| 6,354,989 B1 | 3/2002 | Nudeshima |
| 6,358,195 B1 | 3/2002 | Green et al. |
| 6,361,487 B1 | 3/2002 | Green et al. |
| 6,366,796 B1 | 4/2002 | Yanof et al. |
| 6,387,034 B1 | 5/2002 | Lee |
| 6,387,035 B1 | 5/2002 | Jung, Jr. et al. |
| 6,416,492 B1 | 7/2002 | Nielson |
| 6,454,696 B1 * | 9/2002 | Kindlein et al. ................. 600/7 |
| 6,500,109 B2 | 12/2002 | Tokita et al. |
| 6,512,942 B1 * | 1/2003 | Burdette et al. ............. 600/427 |
| 6,572,525 B1 * | 6/2003 | Yoshizumi ...................... 600/7 |
| 2001/0029334 A1 | 10/2001 | Graumann et al. |
| 2002/0077546 A1 | 6/2002 | Aldefeld et al. |
| 2002/0087080 A1 | 7/2002 | Slayton et al. |

2003/0074011 A1   4/2003   Gilboa et al.

FOREIGN PATENT DOCUMENTS

| EP | 0 424 912 | 5/1991 |
|---|---|---|
| EP | 0 455 439 A2 | 11/1991 |
| WO | WO 91/07726 | 5/1991 |
| WO | WO 96/10949 | 4/1996 |
| WO | WO 96/11624 | 4/1996 |
| WO | WO 96/42070 | 12/1996 |
| WO | WO 98/39736 | 9/1998 |
| WO | WO 00/14668 | 3/2000 |
| WO | WO 00/63658 | 10/2000 |
| WO | WO 01/06924 | 2/2001 |
| WO | WO 01/87164 | 11/2001 |
| WO | WO 01/95795 | 12/2001 |
| WO | WO 02/44749 | 6/2002 |

OTHER PUBLICATIONS

Adams and Bischof; "Seeded Region Growing"; *IEEE Transactions on Pattern Analysis and Machine Intelligence*; Jun. 1994; pp. 641-647; vol. 16, No. 6.

Anuta, P.E., Oct. 1970 IEEE Transactions on Geoscience Electronics, vol. GE-8, No. 4, "Spatial Registration of Multispectrical and Multitemporal Digital Imagery Using Fast Fourier Transform Techniques", pp. 353-368.

Ballard and Brown; *Computer Vision*; 1982; pp. 119-165; Chapters 4-5; Prentice-Hall, Inc., Englewood Cliffs, New Jersey.

Barnea and Silverman, Feb. 1972 IEEE Transactions on Computers, vol. C-21, No. 2, "A Class of Algorithms for Fast Digital Image Registration", pp. 179-186.

Besag; "On the Statistical Analysis of Dirty Pictures"; *Journal of the Royal Statistical Society*; 1986; pp. 259-279; vol. 48, No. 3.

Beveridge, Griffith, Kohler, Hanson and Riseman; "Segmenting Images Using Localized Histograms and Region Merging"; *International Journal of Computer Vision*; 1989; pp. 311-347; vol. 2; Kluwer Academic Publishers, Boston.

Bezdek et al.; "Review of MR image segmentation techniques using pattern recognition"; Medical Physics; vol. 20(4); pp. 1033-1048; 1993.

Brown, L.G., Dec. 1992 ACM Computing Surveys vol. 24 No. 4, "A Survey of Image Registration Techniques", pp. 325-378.

Chakraborty et al.; Deformable boundary finding in medical images by integrating gradient and region information; IEEE Transactions on Medical Imaging; vol. 15; pp. 859-870; 1996.

Cline et al. "3D reconstruction of the brain from magnetic resonance images using a connectivity algorithm"; Magnetic Resonance Imaging; vol. 5; pp. 345-352; 1987.

Cline et al.; "Three-dimensional segmentation of MR images of the head using probability and connectivity"; Journal of Computer Assisted Tomography; vol. 14(6); pp. 1037-1045; 1990.

Cline et al.; "Vascular morphology by three-dimensional magnetic resonance imaging"; Magnetic Resonance Imaging; vol. 7; pp. 45-54; 1989.

Cohen; "On Active Contour Models and Balloons"; *CVGIP: Image Understanding*; Mar. 1991; pp. 211-218; vol. 53, No. 2; Academic Press, Inc.

Collignon, A., et al., Apr. 1995 Proc. of the Xvth Int'l. Conf. On Computer Vision, Virtual Reality, and Robotics in Medicine (CVRMed '95), vol. 905, "Automated Multi-Modality Image Registration Based On Information Theory", pp. 263-274.

Cover and Thomas; *Elements of Information Theory*; 1991; pp. 12-42, 279-332; Chapters 2, 12; John Wiley & Sons, Inc., New York.

Decarli et al.; "Method for quantification of brain, ventricular, and subarachnoid CSF volumes from MR images"; Journal of Computer Assisted Tomography; vol. 16(2); pp. 274-284; 1992.

Delagnes et al.; "Active contours approach to object tracing in image sequences with complex background"; Pattern Recognition Letters; vol. 16(2); pp. 171-178; 1995.

Devroye, Györfi and Lugosi; *A Probabilistic Theory of Pattern Recognition*; 1996; pp. 9-20, 61-90; Chapters 2, 5; Springer-Verlag New York, Inc.

Diallo, B.; "Conception, realisation et exploitation d'une base de donnees en neuroimagerie cognitive"; Universite de Caen/Basse-Normandi; Mar. 1992; pp. 148-180; Caen, France.

Duda, Hart and Stork; *Pattern Classification*; 2001; pp. 20-83, 161-214; Second Edition, Chapters 2, 4; John Wiley & Sons, Inc., New York.

Duda, Hart and Stork; *Pattern Classification*; 2001; pp. 517-599; Second Edition, Chapter 10; John Wiley & Sons, Inc., New York.

Fletcher et al.; A multispectral analysis of brain tissues; Magnetic Resonance in Medicine; vol. 29; pp. 623-630; 1993.

Fukunaga; *Introduction to Statistical Pattern Recognition*; 1990; pp. 51-123; Second Edition, Chapter 3; Academic Press, Inc., San Diego, California.

Geman and Geman; "Stochastic Relaxation, Gibbs Distributions, and the Bayesian Restoration of Images"; *IEEE Transactions on Pattern Analysis and Machine Intelligence*; Nov. 1984, pp. 721-741; vol. PAMI-6, No. 6.

Giardina and Kuhl; "Accuracy of Curve Approximation by Harmonically Related Vectors with Elliptical Loci"; *Computer Graphics and Image Processing*; 1977; pp. 277-285; vol. 6; Academic Press, Inc.

Gomez-Lopera J F et al.: "An analysis of edge detection by using the Jensen-Shannon divergence" Journal of Mathematical Imaging and Vision, vol. 13, No. 1, Aug. 2000, pp. 35-56, XP008033153 Kluwer Academic Publishers, Netherlands ISSN; 0924-9907 the whole document.

Grimmett and Stirzaker; *Probability and Random Processes*; 1992; pp. 1-21; Second Edition, Chapter 1; Oxford University Press, Oxford.

Haralick and Shapiro; "Image Segmentation Techniques"; *Computer Vision, Graphics, and Image Processing*; 1985; pp. 100-132; vol. 29.

He, Hamza and Krim; "An Information Divergence Measure for ISAR Image Registration"; IEEE Workshop on Statistical Signal Processing; Aug. 2001; Singapore.

Hibbard; "Maximum a posteriori Segmentation for Medical Visualization"; IEEE Workshop on Biomedical Image Analysis (WBIA98), Santa Barbara, California; Jun. 1998; pp. 93-102.

Hibbard, et al., Jun. 26, 1987 Science vol. 236, "Three-Dimensional Representation and Analysis of Brain Energy Metabolism", pp. 1641-1646.

Höhne et al.: "Interactive 3D segmentation of MRI and CT volumes using morphological operations"; Journal of Computer Assisted Tomography; vol. 16(2); pp. 285-294; 1992.

Holupka et al.; "Ultrasound image fusions for external beam radiotherapy for prostate cancer"; Int. J. Radiation Oncology Biol. Phys.; vol. 35, No. 5; pp. 975-984; 1996; Elsevier Science Inc., USA.

Kass, Witkin and Terzopoulos; "Snakes: Active Contour Models"; *International Journal of Computer Vision*; 1988; pp. 321-331; vol. 1, No. 4; Kluwer Academic Publishers, Boston.

Kohn et al.; "Analysis of brain and cerebrospinal fluid volumes with MR imaging"; Radiology; vol. 178; pp. 115-122; 1991.

Kuhl and Giardina; "Elliptic Fourier Features of a Closed Contour"; *Computer Graphics and Image Processing*; 1982; pp. 236-258; vol. 18; Academic Press, Inc.

Kullback and Leibler; "On Information and Sufficiency"; *Annals of Mathematical Statistics*; 1951; pp. 79-86; vol. 22.

Kullback; *Information Theory and Statistics*; 1959; pp. 1-35; Chapters 1, 2; Dover Publications, Inc., Mineola, New York.

Lin; "Divergence Measures Based on the Shannon Entropy"; *IEEE Transactions on Information Theory*; Jan. 1991; pp. 145-151; vol. 37, No. 1.

Maes, F., et al., Jun. 1996 IEEE Proceedings of MMBIA, "Multi-Modality Image Registration by Maximization of Mutual Information", pp. 14-22.

Malladi, Sethian and Vemuri; "Shape Modeling with Front Propagation: A Level Set Approach"; *IEEE Transactions on Pattern Analysis and Machine Intelligence*; Feb. 1995; pp. 158-175; vol. 17, No. 2.

McInerney et al.; Deformable models in medical image analysis; Proceedings of Mathematical Methods Biomedical Image Analysis; pp. 171-180; 1996.

Miller et al.; Mathematical textbook of deformable neuroanatomies; Proceedings of the National Academy of Sciences USA; vol. 90; pp. 11944-11948; 1993.

Neal et al.; "Technical Note: Evaluation of a region growing algorithm for segmenting pelvic computed tomography images during radiotherapy planning"; The British Journal of Radiology; vol. 67; pp. 392-395; 1994.

Nocedal and Wright; *Numerical Optimization*; 1999; pp. 10-63; Chapters 2, 3; Springer-Verlag New York, Inc.

Pal and Pal; "A Review on Image Segmentation Techniques"; *Pattern Recognition*; 1993; pp. 1277-1294; vol. 26, No. 9; Great Britain.

Pelizzari, C.A., et al., Jan./Feb. 1989 Journal of Computer Assisted Tomography, vol. 13, No. 1, "Accurate Three-Dimensional Registration of CT, PET, and/or MR Images of the Brain", pp. 20-26.

Pietrzuk, U. et al.; "An Interactive technique for three-dimensional image registration: validation for PET, SPECT, MRI and CT brain studies"; The Journal of Nuclear Medicine; vol. 35, No. 12; Dec. 1994; pp. 2011-2018.

Pietrzuk, U. et al.; "Three-dimensional alignment of functional and morphological tomograms"; Journal of Computer Assisted Tomography; Jan.-Feb. 1990; vol. 14, No. 1; pp. 51-59; USA.

Pratt, W.K., May 1974 IEEE Transactions on Aerospace and Electronic Systems, vol. AES-10, No. 3, "Correlation Techniques of Image Registration", pp. 353-358.

Press, Teukolsky, Vetterling and Flannery; *Numerical Recipes in C++, The Art of Scientific Computing*; 2002; pp. 398-429; Second Edition; Chapter 10; Cambridge University Press, Cambridge, UK.

Principe; Xu and Fisher; "Information-Theoretic Learning" in *Unsupervised Adaptive Filtering*; 1999; pp. 265-319; Wiley, New York.

Rényi; "On Measures of Entropy and Information"; *Proceedings of the Fourth Berkley Symposium on Mathematical Statistics and Probability*; Berkeley, California, Jun.-Jul. 1960; Published 1961; pp. 547-561; vol. I; University of California Press.

Rényi; "Some Fundamental Questions of Information Theory"; *Selected Papers of Alfred Rényi*; 1976; pp. 526-552; vol. 2; Akademia Kiado, Budapest.

Rosenman, J.G., et al., 1998 Int. J. Radiation Oncology Biol. Phys., vol. 40, No. 1, "Image Registration: An Essential Part of Radiation Therapy Treatment Planning", pp. 197-205.

Rosenfeld and Kak; Digital Picture Processing; 1982; pp. 55-190; Second Edition, vol. 2, Chapter 10; Academic Press, New York.

Shannon; "A Mathematical Theory of Communication"; *The Bell System Technical Journal*; Jul. Oct. 1948; pp. 379-423, 623-656; vol. 27.

Staib and Duncan; "Boundary Finding with Parametrically Deformable Models"; *IEEE Transactions on Pattern Analysis and Machine Intelligence*; Nov. 1992; pp. 1061-1075; vol. 14, No. 11.

Studholme, C., et al., 1996 Medical Image Analysis, vol. 1, No. 2, "Automated 3-D Registration of MR and CT Images of the Head", pp. 163-175.

Tang and Ma; "General Scheme of Region Competition Based on Scale Space"; *IEEE Transactions on Pattern Analysis and Machine Intelligence*; Dec. 2001; pp. 1366-1378; vol. 23, No. 12.

Toennies, K. D. et al.; "Registration of 3D objects and surfaces"; IEEE Computer Graphics and Applications; vol. 10, No. 3; May 1, 1990; pp. 52-62; New York.

Unal G et al.: "Active polygons for object tracking" proceedings First International Symposium on 30 Data Processing Visualization and Transmission, Padova, Italy, Jun. 19-21, 2002, Jun. 19, 2002, pp. 696-699, XP002290194 2002, Los Alamitos, CA, USA, IEEE Comput. Sox. USA ISBN: 0-7695-1521-5 sections 2.3.

Vaidyanathan et al.; "Comparison of supervised MRI segmentation methods for tumor volume determination during therapy"; Magnetic Resonance Imaging; vol. 13(5); pp. 719-728; 1995.

Van Den Elsen, P.A., et al., Mar. 1993 IEEE Engineering in Medicine and Biology, "Medical Image Matching—A Review with Classification", pp. 26-39.

Van Herk, M., et al., Jul. 1994 Medical Physics, vol. 21, No. 7, "Automatic Three-Dimensional Correlation of CT-CT, CT-MRI, and CT-SPECT Using Chamfer Matching", pp. 1163-1178.

Van Trees; *Detection, Estimation, and Modulation Theory, Part I Detection, Estimation, and Linear Modulation Theory*; 1968; pp. 19-165; Chapter 2; John Wiley & Sons, Inc., New York.

Viola, P., et al. Jun. 1995 Proc of the Vth Int'l Conf. On Computer Vision, "Alignment by Maximization of Mutual Information", pp. 16-23.

Wells et al.; "Adaptive segmentation of MRI data"; IEEE Transactions on Medical Imaging; vol. 15, No. 4; pp. 429-442; 1996.

Witten and Frank; *Data Mining, Practical Machine Learning Tools and Techniques with Java Implementations*; 2000; pp. 157-227; Chapter 6; Morgan Kaufmann Publishers, San Francisco, California.

Yin et al.; "Comparison of bilateral-subtraction and single-image processing techniques in the computerized detection of mammographic masses"; Investigative Radiology; vol. 28(6); pp. 473-481; 1993.

\* cited by examiner

TO FIG. 3B

```
std::list<Anatomy*>
TResponseTableEntry<GENERIC>
TResponseTableEntry<GENERIC>
std::list<double*>
std::list<SeedType*>
TResponseTableEntry<GENERIC>
std::list<Catheter*>
TResponseTableEntry<TFileFrameViewWindow>
TResponseTableEntry<ZDialog>
TResponseTableEntry<TDirectViewWindow>
TResponseTableEntry<TPasswordDisplay>
std::deque<ImageControl*>
std::queue<ImageControl*,std::deque<ImageControl*>>
string
TRegexp
TSubString
streambuf
TStandardAllocator
TVoidPointer
TStreamableTypes
TPWrittenObjects
TPReadObjects
TResId
TDropInfo
TStatus
TModuleProc
TAppDictionary
TAppDictImp
TCommandEnabler
GENERIC
TColor
TFile
TClipboard
BlobManager
Point3D
TPageSupport
TMVectorIteratorImp<TPWrittenObjects::TPWObj,TStandardAllocator>
TMVectorIteratorImp<TStreamableBase*,TStandardAllocator>
```

FIG. 12G

```
TResponseTableEntry<GENERIC>
TResponseTableEntry<TApplication>
TResponseTableEntry<TWindow>
TResponseTableEntry<TFrameWindow>
TResponseTableEntry<TMDIChild>
TResponseTableEntry<TMDIClient>
TResponseTableEntry<TMDIFrame>
TResponseTableEntry<TLayoutWindow>
TResponseTableEntry<TDecoratedFrame>
TResponseTableEntry<TDecoratedMDIFrame>
TResponseTableEntry<TDialog>
TResponseTableEntry<TControl>
std::allocator<std::list<RTBaseObject*>::list_node>
std::allocator<RTBaseObject*>
std::allocator<std::list<RTBaseObject*>::list_node_buffer>
std::allocator<unsigned int>
std::allocator<double>
TResponseTableEntry<TGauge>
TResponseTableEntry<TIsoLevelWindow>
std::allocator<std::list<Seed*>::list_node>
std::allocator<Seed*>
std::allocator<std::list<Seed*>::list_node_buffer>
std::allocator<std::list<Pixel*>::list_node>
std::allocator<Pixel*>
std::allocator<std::list<Pixel*>::list_node_buffer>
std::list<Point3D*>
std::allocator<std::list<Contour*>::list_node>
std::allocator<Contour*>
std::allocator<std::list<Contour*>::list_node_buffer>
std::allocator<std::list<Catheter*>::list_node>
std::allocator<Catheter*>
std::allocator<std::list<Catheter*>::list_node_buffer>
std::allocator<std::list<GuideHole*>::list_node>
std::allocator<GuideHole*>
std::allocator<std::list<GuideHole*>::list_node_buffer>
std::allocator<std::list<Point3D*>::list_node>
std::allocator<Point3D*>
std::allocator<std::list<Point3D*>::list_node_buffer>
```

FIG. 12H

```
std::allocator<ImageCo,  :ol*>
std::allocator<ImageControl**>
TResponseTableEntry<GENERIC>
TLayoutMetrics
PatientDB
TCelArray
TTooltip
TResponseTableEntry<TStatic>
TResponseTableEntry<TButton>
TResponseTableEntry<TCheckBox>
TResponseTableEntry<TRadioButton>
TResponseTableEntry<TDlgFileSource>
TProfile
TResponseTableEntry<TDlgVideoSource>
SetupDB
SeedType
std::list<string*>
std::allocator<std::list<string*>::list_node>
std::allocator<string*>
std::allocator<std::list<string*>::list_node_buffer>
TResponseTableEntry<TDlgAdmin>
TResponseTableEntry<TDlgSystem>
TResponseTableEntry<TDlg2D>
tpid
typeinfo
TResponseTableEntry<DlgChooseContour>
TRegKeyIterator
TRegKey
TCmdLine
TResponseTableEntry<TDlg3D>
TResponseTableEntry<GENERIC>
Dvh
TResponseTableEntry<GENERIC>
TResponseTableEntry<TBrachyWindowView>
TResponseTableEntry<CDVGraphWindow>
TResponseTableEntry<DVDialog>
TResponseTableEntry<DataElementPage>
TResponseTableEntry<TitleElementPage>
```

FIG. 12I

```
TResponseTableEntry<Ax. ElementPage>
DVDialogBuffer
DataElementBuffer
CChartTools
TitleElementBuffer
AxisElementBuffer
TDocManager
TDocTemplate
NeedleStructure
std::list<string*>
TProjectRCVersion
TResponseTableEntry<GENERIC>
TNotify
TResponseTableEntry<TZeroSetDisplay>
TMVectorIteratorImp<string,TStandardAllocator>
TVideoControls
TFrameGrabber
TResponseTableEntry<PeripheralLoad>
TScroller
Transformation
ImageControl
AnatomyList
SeedType
std::list<Point3D*>
std::list<Contour*>
std::allocator<std::list<Anatomy*>::list_node>
std::allocator<Anatomy*>
std::allocator<std::list<Anatomy*>::list_node_buffer>
std::allocator<std::list<double*>::list_node>
std::allocator<double*>
std::allocator<std::list<double*>::list_node_buffer>
std::allocator<std::list<SeedType*>::list_node>
std::allocator<SeedType*>
std::allocator<std::list<SeedType*>::list_node_buffer>
TResponseTableEntry<TNeedleViewWindow>
TResponseTableEntry<TAllViewWindow>
std::list<Dose*>
std::allocator<std::list<Dose*>::list_node>
```

FIG. 12J

```
std::allocator<Dose*>
std::allocator<std::list<Dose*>::list_node_buffer>
TResponseTableEntry<TGadgetWindow>
TResponseTableEntry<TTinyCaption>
TResponseTableEntry<TFloatingFrame>
TResponseTableEntry<TDockableGadgetWindow>
TResponseTableEntry<TFloatingSlip>
TResponseTableEntry<TEdgeSlip>
TResponseTableEntry<THarbor>
TResponseTableEntry<TCommonDialog>
TResponseTableEntry<TPrintDialog>
TResponseTableEntry<TPrinterAbortDlg>
TResponseTableEntry<TRecentFiles>
TResponseTableEntry<TEdit>
TResponseTableEntry<TFindReplaceDialog>
TResponseTableEntry<TEditSearch>
TResponseTableEntry<TOpenSaveDialog>
TResponseTableEntry<TEditFile>
TResponseTableEntry<TPreviewPage>
TResponseTableEntry<TApxPreviewWin>
TResponseTableEntry<KitDataDialog>
TResponseTableEntry<StepperDefinition>
TResponseTableEntry<ProbeDefinition>
TResponseTableEntry<UltraSoundDefinition>
TResponseTableEntry<RecordSelector>
TResponseTableEntry<TPropertyPage>
TResponseTableEntry<GuideDataPage>
TResponseTableEntry<GuideBaseDataPage>
TResponseTableEntry<GuideDataDisplay>
TResponseTableEntry<TWindowView>
TResponseTableEntry<TScrollBar>
TResponseTableEntry<TSlider>
TResponseTableEntry<TImageWindow>
TResponseTableEntry<TVideoControlsDisplay>
TResponseTableEntry<TDefaultsWindow>
std::list<string*>
TResponseTableEntry<TBrachyApp>
std::list<int>
```

FIG. 12K

RCVersion
TableEntry<GENERIC>

TableEntry<TRichEdit>
TableEntry<THelpFileManager>
TableEntry<TDragListEventHandler>
TableEntry<TDragList>
TableEntry<TColumnHeader>
IteratorImp<TColumnHeader::TItem,TStandardAllocator>
TableEntry<TVbxControl>
TableEntry<TVbxEventHandler>
TableEntry<TTabControl>
ion<TTabEntryInternal>
TableEntry<TUpDown>
TableEntry<GENERIC>
TableEntry<TStatusBar>
TableEntry<TSplashWindow>
TableEntry<TRollDialog>
TableEntry<TPreviewWin>
TableEntry<TPickListDialog>
TableEntry<TPaneSplitter>
eratorImp<TVoidPointer,TStandardAllocator>
TableEntry<TSplitter>
TableEntry<TOleLinkView>
TableEntry<TOleView>
TableEntry<TOleMDIFrame>
TableEntry<TOleFrame>
TableEntry<TOleWindow>
TableEntry<TMciHiddenWindow>
TableEntry<TListView>
TableEntry<TEditView>
TableEntry<TDocManager>
TableEntry<TClipboardViewer>
TableEntry<TChooseFontDialog>

TableEntry<TPlanDocumentWindow>
TableEntry<GENERIC>

FIG. 12L

TRegFormatHeap
TResponseTableEntry<TShowTableWindow>
TResponseTableEntry<PeripheralLoad>
TLogger
Con3D
TResponseTableEntry<TThreeDWindow>
D3DUtil
Input
D3DView
Con3DDose
Con3DAnat
TCriticalSection

FIG. 12M

REAL TIME BRACHYTHERAPY SPATIAL REGISTRATION AND VISUALIZATION SYSTEM

CROSS-REFERENCE AND PRIORITY CLAIMS TO RELATED APPLICATIONS

This patent application is a continuation of U.S. application Ser. No. 09/573,415 filed on May 18, 2000, now U.S. Pat. No. 6,512,942, which is a continuation of U.S. application Ser. No. 09/087,453 filed on May 29, 1998, now U.S. Pat. No. 6,129,670, which is a continuation-in-part of U.S. application Ser. No. 08/977,362 filed on Nov. 24, 1997, now U.S. Pat. No. 6,256,529.

CROSS-REFERENCE TO COMPUTER PROGRAM LISTING ON COMPACT DISC

This patent application includes a Computer Program Appendix on compact disc.

BACKGROUND AND SUMMARY OF THE INVENTION

The present invention is directed in general to an improved method and apparatus for carrying out minimally invasive treatments of the human body by virtual reality visualization of the treatment area. More particularly the invention is concerned with use of an apparatus and method for providing real time images of a human anatomy undergoing treatment along with rapid radiation seed therapy planning and rapid performance of therapy including an automatic seed loading methodology which enhances therapeutic treatment with greatly improved efficiency both in terms of time and resources.

New minimally invasive surgical procedures are most often optically guided, but such optical guidance methods do not permit visualization and guidance of instruments or probes within (inside) the target tissue or organ. Incorporation of real-time three-dimensional visualization inside diseased tissues would provide accurate guidance of therapy. Open-magnet MRI is used to visualize some procedures such as thermal therapy and brain biopsies. However, the method is expensive, not truly real-time, and is limited in application.

Numerous conventional treatment methods involve attempts to provide a targeted dosage of radiation or chemicals to the organ, and such treatments are often based on general anatomical assumptions of size and location. These methods suffer from inaccuracy of localizing the target for any one particular individual and potential real time changes of relative orientation and position of target tissue, normal tissue, and radiation therapy devices.

It is instructive in explaining the invention to consider one specific type of exemplary condition, adenocarcinoma of the male prostate which is the most commonly diagnosed cancer in the male population of the United States. At present, 254,000 new cases of prostate cancer were diagnosed in 1995 and 317,000 in 1996. In the 1960s, a method of implanting radioactive gold or iodine seeds was developed. With this approach, the radioactive material is permanently placed into the prostate via a retropubic approach during laparotomy when diagnostic lymphadenectomy was also being performed. A high dose of radiation is delivered to the prostate as the radioactive seeds decay. In several reports, the five year disease free survival ("local control") obtained by this method was compared to similarly staged patients treated with an external radiation beam. In view of this, gold was replaced by $I^{125}$ implantation for safety of personnel doing implantation. Except for early stage prostate cancer (T2a tumors), inferior rates of local control are reported with "free hand" 125-Iodine implantation. There was significant dose inhomogeneity due to the nonuniformity of seed placement, leading to underdosing of portions of the prostate gland and significant complications due to overdosing of adjacent healthy tissue structures. The poor results for local control and normal tissue complication were attributed to the doctor's inability to visualize and hence control where the radioactive seeds were actually being deposited inside the patient.

Recently, transrectal ultrasonography ("TRUS") has been used to visualize 125-Iodine seed placement during transperineal implantation. The early reported rates of serious late complications is higher than external beam therapy. Even with this technique, significant imprecisions in seed placement are observed. Due to the proximity of the prostate to the rectum and bladder, incorrect seed placement may lead to serious overdosing of these structures and late complications.

The recent transrectal ultrasound guided transperineal implant technique has been developed which is in use. That procedure is described in three steps: (1) the initial volumetric assessment of the prostate gland performed using ultrasound, (2) development of a radiation therapy "preplan," and (3) performing the actual intraoperative implant. The purpose of the initial volumetric assessment prior to the pre-plan or implantation is to obtain a quantitative understanding of the size of the prostate, which is then used to determine the total activity and distribution of radioactivity which is to be implanted into the prostate. To perform the assessment, an ultrasound probe is physically attached to a template. The template is a plastic rectangle which contains an array of holes separated at predefined intervals, usually 5 mm. The template system serves two purposes: (1) to fix the ultrasound probe, and hence the imaging plane to the reference frame of the catheter and seed positions, and (2) to guide the catheters into the prostate volume. More specifically, the template system serves as a reference frame for spatial quantities which are required for the description of the implant procedure. Using transrectal ultrasound, a number of serial ultrasound images are obtained at 5-mm intervals, and the prostate is outlined on each image. The images are taken so that the entire prostate gland is covered. This results in a stack of two-dimensional outlines, or contours, which, taken together, outline the entire three-dimensional prostate volume. From this volume, the quantitative volume of the prostate is calculated.

Once the three-dimensional contour data has been obtained for the prostate volume, a radiation therapy plan which describes the positions of the radioactive seeds within the prostate is developed. This plan attempts to optimize the dose to the prostate, minimize the dose to surrounding healthy tissue, and minimize dose inhomogeneity. The positions of the radioactive seeds are constrained to fall within the catheter tracks, since the seeds are placed within the prostate transperineally via these catheters. The result of the pre-plan describes the positions and strengths of the radioactive seeds within the catheter which optimizes the dose to the prostate.

Intraoperatively, the TRUS probe is inserted, and the template is mounted against the perineum. As previously described, the template is a plastic rectangle which contains an array of holes separated at fixed intervals. These holes act as guides for the catheters. The TRUS probe is inserted into the rectum and placed so that the image corresponds to the prostate base (the maximum depth). Two or three catheters are inserted into the tissue surrounding the prostate or in the periphery of the prostate to immobilize the gland. These catheters contain no radioactive seeds. This image serves as a spatial reference for all further images and seed positions within the prostate. Subsequently, catheters are inserted into the gland based on the pre-plan through the template. The ultrasound probe is positioned each time so that the catheter, and hence seeds, which are inserted into the prostate are visible on the ultrasound image. If the placement of the catheter within the prostate is not according to the pre-plan, the catheter is then withdrawn and reinserted until the catheter is correctly placed. This is a time-consuming process; and it is very difficult to achieve optimal placement. Invariably, the catheters deflect angularly as they are inserted, and their positions are difficult to determine by two-dimensional ultrasound. This is due to the fact that the visualization process is a two-dimensional process while the actual implant procedure is three-dimensional. Once all the seeds are in place, another series of two-dimensional images are obtained to quantify the final, resultant dose distribution delivered to the patient. In some instances, a pair of orthogonal fluoroscopic images are also obtained to determine the final seed placements. This procedure is usually performed a few weeks post implant.

These above described prior art systems suffer from inherent inaccuracy, the inability to correct the positioning of the radioactive seeds without repeated withdrawal and reinsertion of seeds into the prostate and are not real time manipulations of the therapeutic medium. Further, the overall positioning of the template and patient may be different during treatment compared to the assessment phase. Consequently, the catheter position and seed position may be at an undesired position relative to the presumed assessment phase location.

It is therefore an object of the invention to provide an improved system and method for invasive treatment of the human body.

It is another object of the invention to provide a novel system and method for real time and/or near real time, three-dimensional visualization of a human organ undergoing invasive treatment.

It is also an object of the present invention to provide a more precise and accurate implant placement for radiation therapy, thermal therapy, and surgical ablation.

It is also an object of the invention to provide an improved system and method for generating a three-dimensional image data set of a human organ for a treatment protocol using a real-time ultrasound imaging system with spatial landmarks to relate the image data set to present time, invasive treatment devices.

It is a further object of the invention to provide a novel system and method for spatial registration of two-dimensional and three-dimensional images of a human organ, such as the human prostate, with the actual location of the organ in the body.

It is an additional object of the invention to provide an improved method and system for three-dimensional virtual imaging of the male prostate gland and overlaid virtual imaging of devices being inserted into the prostate for deposition of radioactive seeds for cancer therapy.

It is yet a further object of the invention to provide an automated method and system for loading of radioactive therapeutic treatment seeds based on a clinical plan enabling rapid treatment based on substantially real time pre-planning using rapid patient organ evaluation.

These and other objects and advantages of the invention will be readily apparent from the following description of the preferred embodiments thereof, taken in conjunction with the accompanying drawings described below.

BRIEF DESCRIPTION OF THE DRAWINGS

FIGS. 12A–12M illustrate flow diagrams of software module operative connections;

DETAILED DESCRIPTION OF PREFERRED EMBODIMENTS

Figure 1:
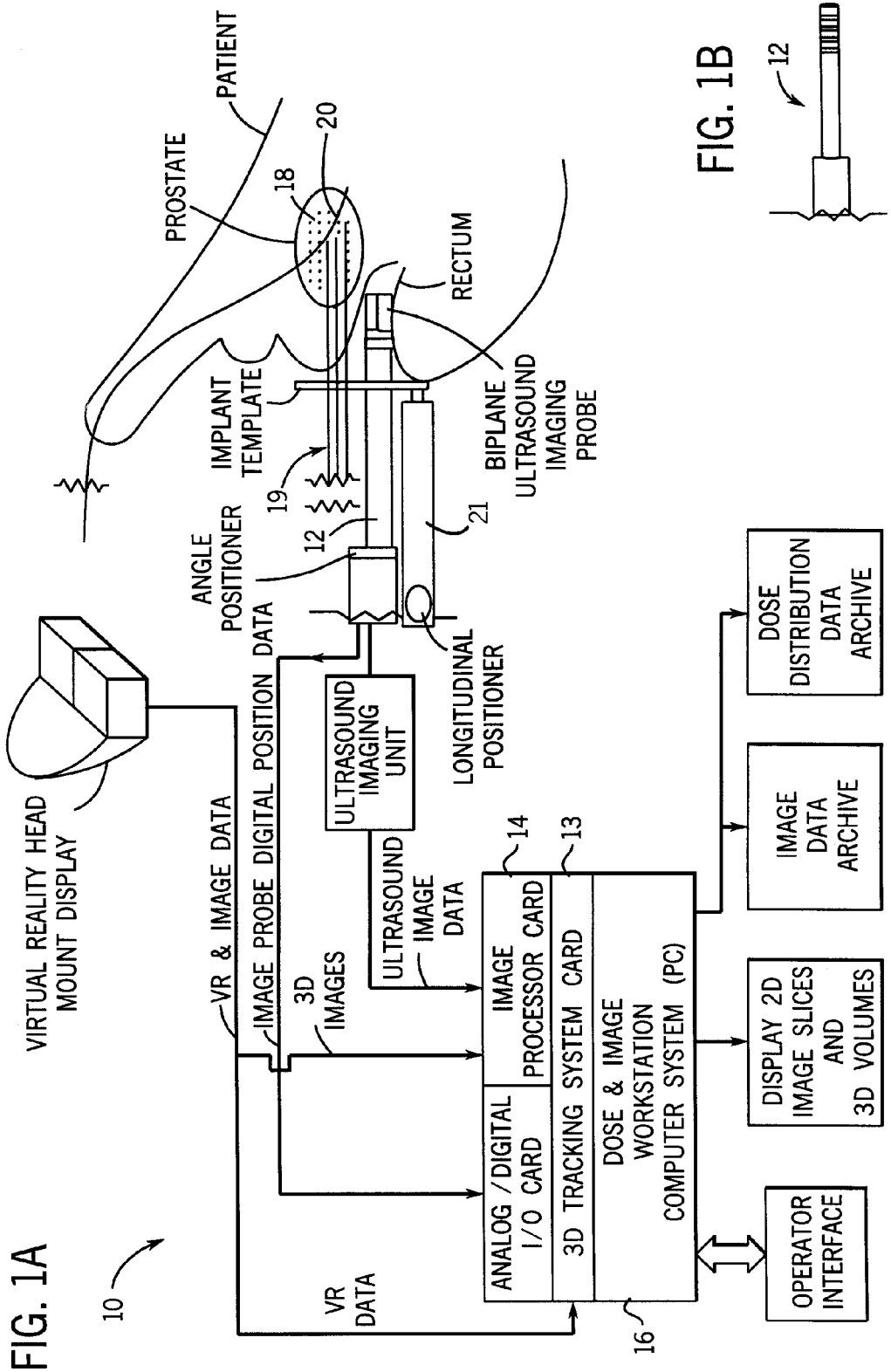
FIG. 1A illustrates a block diagram of an embodiment of the invention and FIG. 1B shows an alternate embodiment for a three-dimensional probe.

A system 10 constructed in accordance with an example of the invention is illustrated generally in FIG. 1A. A three-dimensional probe 12 accumulates image data from a treatment region or organ of a patient, image data is processed using a three-dimensional imaging card 14. The probe 12 preferably is an ultrasound device but can be any other rapid imaging technology, such as rapid CT or MR. A conventional personal computer 16 having a monitor can be used to operate on the image data from the imaging card 14 using conventional software and hardware tools to be described in more detail hereinafter. Radioactive seeds 18 are provided for insertion using any one of a variety of conventional means for inserting devices or articles into the human body, such as insertion devices 19, which may be either needles or stiff catheters. The three-dimensional ultrasound probe 12, therefore, provides an image signal to the computer 16 and a virtual reality interface card 13 coupled to the imaging card 14 which enables a user to visualize a translucent image of the patient organ and real time interaction of any one of a variety of treatment devices, such as the implant needles 19 or a Foley catheter 20, and one of the seeds 18 within the organ. Computer software can be utilized in a conventional manner to visualize the three-dimensional imaging data in various formats (see the Computer Program Listing Appendix and discussion hereinafter). The formats include orthogonal two dimensional images, oblique two-dimensional images, and translucent three-dimensional rendering. All of these reconstructions can be directly displayed on the computer monitor; and three-dimensional translucent, stereoscopic, rendering is also available in the VR (Virtual Reality) mode.

One of the preferred ultrasound probe 12 for example, is a conventional Kretz ultrasound imaging system manufactured by Kretz Corporation, now available as Medison Combison 530 through Medison America Corporation, Pleasantown, Calif. This system and other such conventional systems are readily available and can provide real time ultrasound image data. The Medison Combison ultrasound system incorporates an endorectal probe which acquires multiple image planes in real time and in certain embodiments the software (see the Computer Program Listing Appendix) reconstructs the translucent three-dimensional volume. Another example is of a B&K Leopard ultrasound imaging system with endorectal imaging probe (Boston, Mass.). Alternate systems include biplanar two-dimensional imaging systems with the probe mounted in a stepper motor driven holder for rapid automatic acquisition of multiple image planes.

In a most preferred form of the invention, the system 10 includes computer software for real-time image acquisition, image contouring, dose calculation and display software, dose volume histograms, three-dimensional dose contours, post-implant seed localization, and the patient scheduling spreadsheet software. The Computer Program Listing Appendix of computer software shows how to implement these functionalities. FIGS. 12A–M illustrates the operative connection between modules of the software. The system software enables a two-dimensional and three-dimensional image visualization for brachytherapy employing two-dimensional ultrasound imaging for use in radioactive seed implants of the prostate. The software for the brachytherapy seed implant and dose calculation system was developed on a Pentium-based processor with supporting graphics and digitizing hardware. The software consists of two-dimensional and three-dimensional routines. The two-dimensional tools consist of standard imaging tools largely available for CT and MRI applications. These tools include displays of the imaging volume in any of the three standard orthogonal planes (transverse, sagittal, and coronal), in addition to the ability to display the imaging in any arbitrary, oblique imaging plane. Standard image processing tools such as real time window leveling, zoom and pan will be available. The three-dimensional tools consist of a three-dimensional rendering of the actual contour slices imaging data. Based upon volumetric patient studies, the prostate volume can be displayed. The user has the option of viewing one or a mixture of two-dimensional and three-dimensional surface views on the monitor.

Contouring tools are also available for the user to draw with the mouse outlines, or contours, of any structure visible on the imaging plane. Each contour can be varied as to color, line thickness, and line pattern to aid in distinguishing between different contour sets.

Once a set of two-dimensional contours has been defined, either manually or automatically, on a number of different image slices they can be reconstructed in real time in the three-dimensional translucent view (described in more detail hereinafter). This results in a surface rendering of the volume bounded by the contours. The surface rendering can be chosen to be transparent, solid, or invisible (not rendered at all).

Once a seed has been placed into treatment position (details concerning seed implantation provided later), the user has the ability to display the dose of one or a set of seeds. The dose as a function of position for a cylindrical $^{125}$I or $^{103}$Pd seed of a given activity can be determined from a lookup table or calculated from an analytic formula. The dose field can be visualized as a set of isodose lines in two-dimensions or isodose surface in three-dimensions. The process of constructing an isodose line or surface is defined by simply drawing a point for each pixel/voxel which contains a certain specified dose value. For example, the user can specify that the 137 Gy, 120 Gy, 100 Gy, and 60 Gy isodose lines be drawn on the two-dimensional slice for each image plane, and the 137 Gy isodose surface shown on the three-dimensional rendered mode. Again, similar to the contoured volumes, the isodose surface can be reconstructed in any of the user selected modes defined for contoured volumes.

The features/capabilities of the system software functionalities include: complete patient database archive and dose plan "playback"; external image import capability; look-up tables for multiple seed kits and template guides; multiple ultrasound imaging machine configuration capability; image slice contouring using mouse, with edit capability; image cropping, image sizing, tiling, cascading; three-dimensional display of prostate, urethra, and other anatomies; rapid "on-line" dose calculation in operating room/cysto suite during procedure; dose display with isodose lines, three-dimensional translucent, and dithered isodoses; image export and printing (dose slices, contour slices, etc.); seed implant plan export and printing; dose volume histograms (with export and printing); three-dimensional image support including three-dimensional image reconstruction from slices; three-dimensional display of isodose surfaces; image slice selection from three-dimensional image through any transverse plane; post-implant assessment including automatic seed localization; computer-controlled stepper; selection of manual (mouse entry), semi-automatic (button push), or full automatic (computer-controlled stepper) ultrasound image collection.

For collecting ultrasound image data, the diagnostic transrectal ultrasound probe 12 (see FIG. 2) is inserted into the patient's rectum to obtain real time volumetric images of the prostate for use during the implant procedure. The diagnostic probe 12 is preferably a phased array probe designed so that the array of transducers can rotate about the axis of the array sweeping out a three-dimensional imaging volume. As the probe 12 rotates, images are captured and digitized by use of the imaging card 14 (see FIG. 1A), so as to create a fixed number of images slices per rotation. An alternative method utilizes a transverse oriented phased array form of the endorectal probe 12 which is moved longitudinally in an automated rapid sequence so as to create a series of transverse image slices automatically. Another embodiment of the probe 12 can incorporate multiple transverse phased arrays (shown in phantom in FIG. 1B) arranged parallel to each other orthogonal to the axis of an endorectal probe to produce multiple simultaneous image slices (see, for example, FIGS. 5A and 5B). The three-dimensional image data will be represented as a three dimensional image raster.

Figure 2:
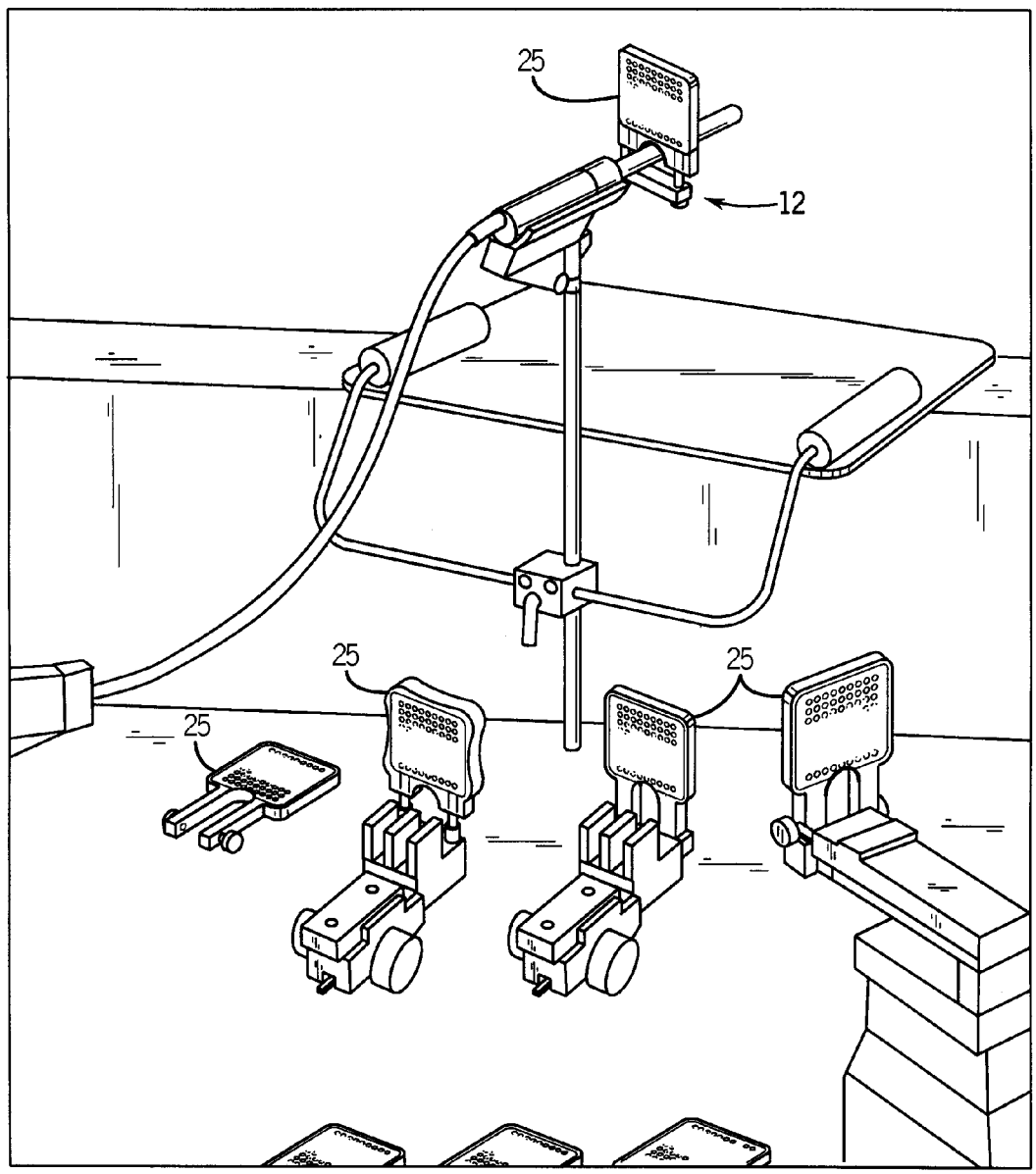
FIG. 2 illustrates an ultrasound guided implant system.
Figure 3A:
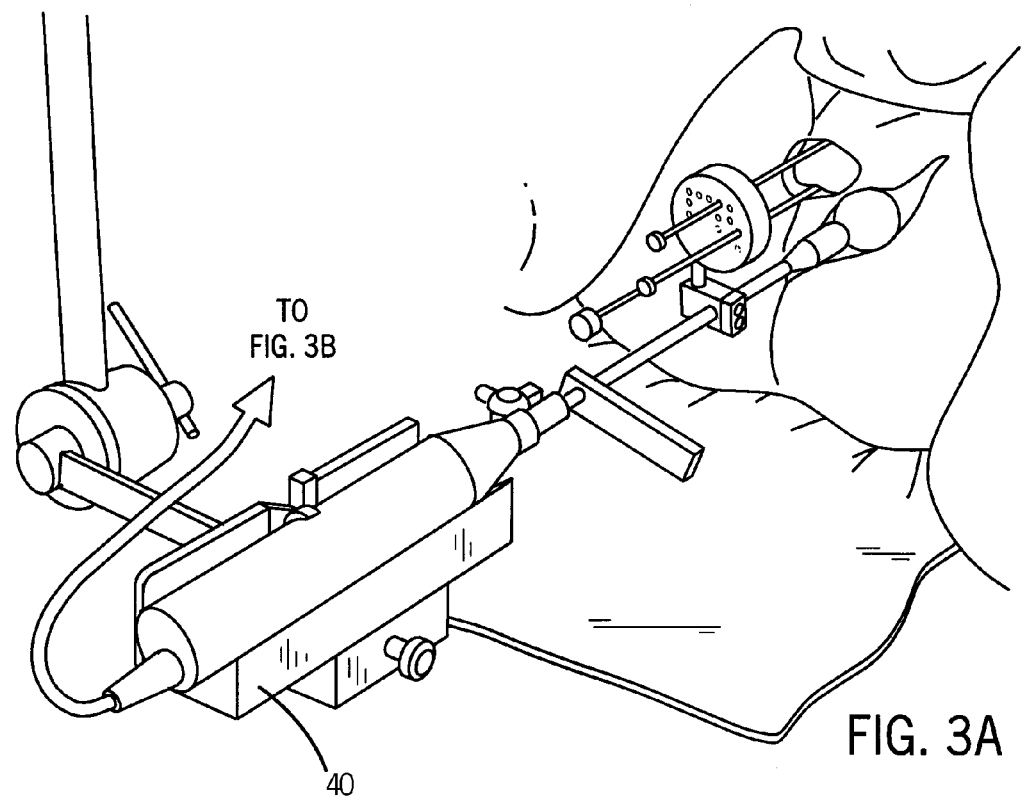
FIG. 3A illustrates patient setup for a radioactive implant procedure.
Figure 3B:
FIG. 3B illustrates an anatomical prostate phantom used for testing and planning.
Figure 3C:
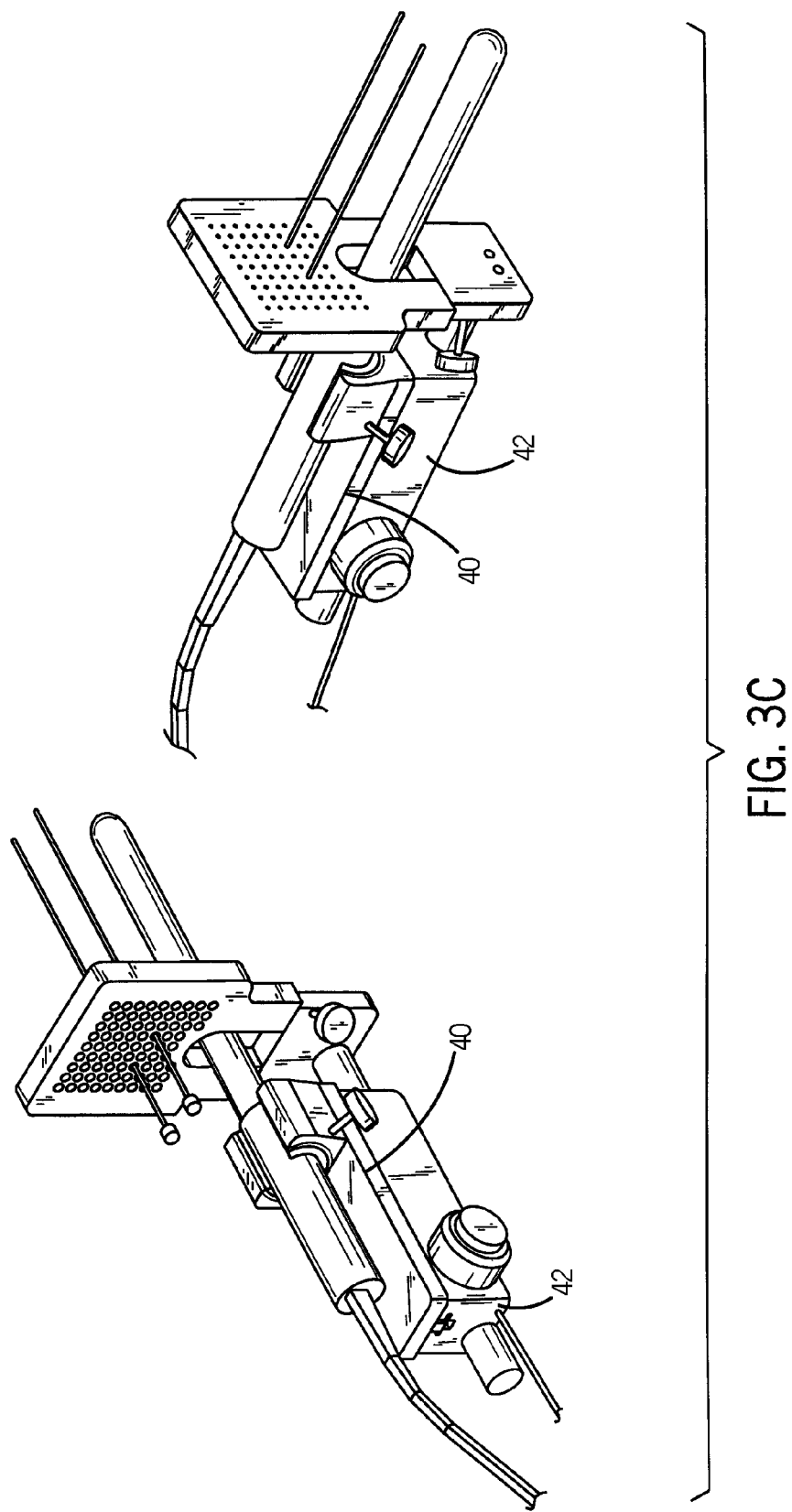
FIG. 3C illustrates in detail a probe holder/stepper assembly shown partly in FIG. 3A.

The ultrasound probe 12 can be mounted into a probe holder 40 (see FIGS. 3A and 3C) with FIG. 3B illustrating one example of an ultrasound image from an anatomical prostate phantom employed to carry out testing and planning. The probe holder 40 includes a digital encoder 42 for providing information regarding the position of all of the desired ultrasound image planes in the prostate relative to each other. The image plane location will be automatically sent to the system computer and "tagged" to the acquired ultrasound image for that position (FIG. 2). Thus, it will be possible to reproduce the longitudinal and lateral positions of the implant catheters for the ultrasound therapy applicators and for the temperature probes.

Figure 13A:
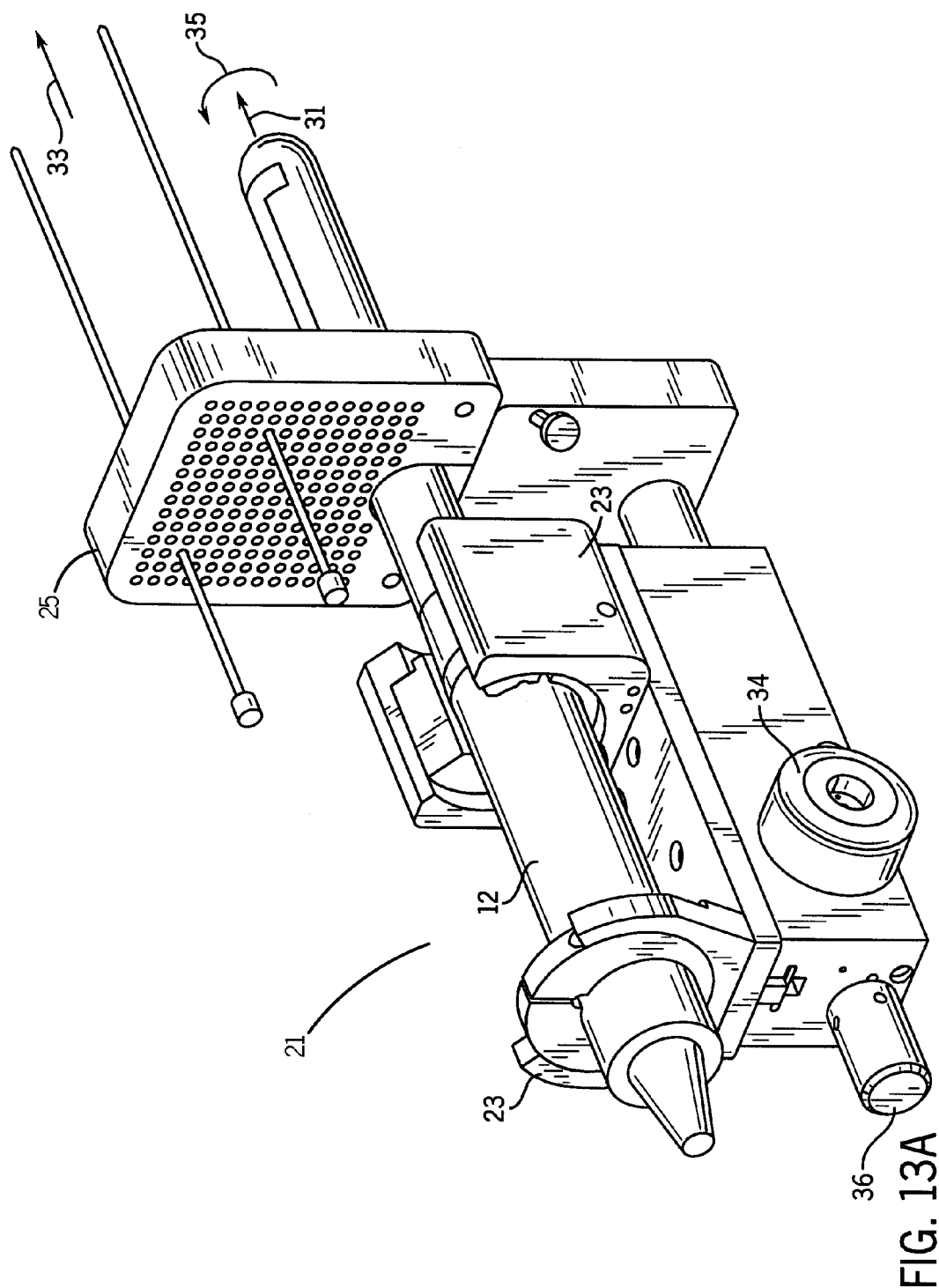
FIG. 13A illustrates a perspective view of a stepper assembly with the probe in position and FIG. 13B illustrates a perspective view of the probe stepper along with a probe stabilization system.

A probe holder/stepper assembly 21 (see FIG. 1A and in particular FIGS. 13A and B) accommodates most ultrasound endorectal probes from various manufacturers. A "collett" 23 surrounds the probe 12 and is inserted into the stepper/probe holder assembly 21. The stepper 21 is a digital device with an automatic imaging link to the ultrasound machine and to the remainder of the system 10. The stepper 21 has three digitally encoded axes: main probe stage longitudinal axis 31, needle insertion template longitudinal axis 33, and the rotational axis 35 of the imaging probe itself. The stepper 21 automatically records the longitudinal (z-axis) position and sends that information to the computer 16. Whenever the user desires to acquire an image plane, the spatial position of that image plane is automatically registered with that image. Thus, it requires less than a minute to digitally acquire and document all the image planes in a typical volume study. The stepper 21 can be incrementally moved by the user with stepper knob 34 and the template 25 can be stepped by template positioning control 36.

Figure 4A:
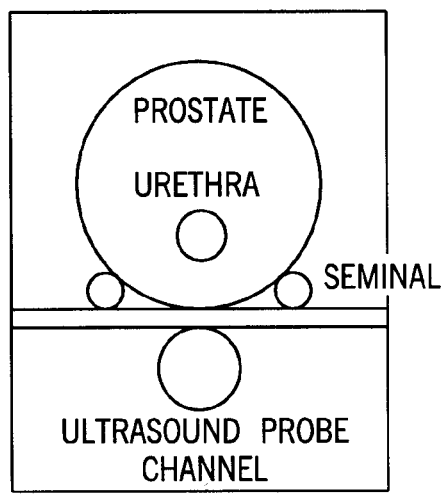
FIG. 4A illustrates a front schematic view of a brachytherapy phantom and FIG. 4B a side schematic view of the brachytherapy phantom.
Figure 4B:
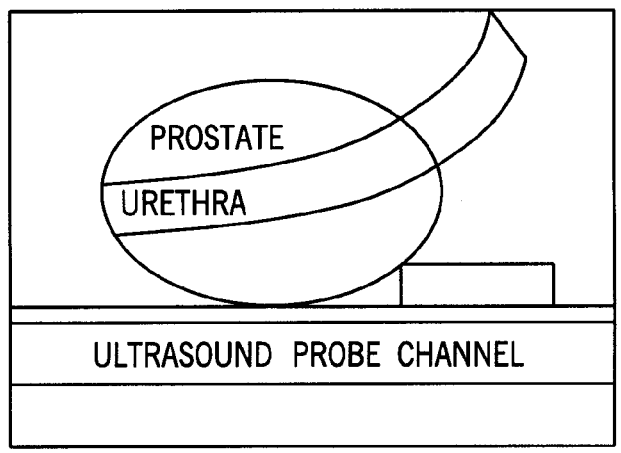

The holder/stepper assembly 21 can move the probe 12 in 2.5 mm increments. A transrectal probe from B&K was used which operates at a frequency of 7.5 MHz and contains two sets of 128 transducer elements forming both transverse and sagittal imaging assays. The imaging probe 12 was moved via a knob on the side of the stepper 21 and its position measured via a digitally interfaced optical position encoder. The probe holder/stepper 21 with transrectal probe 12 mounted is shown in FIG. 1. The real time multi-plane ultrasound probe 12 was modeled by obtaining single digitized transverse images at either 2.5 or 5 mm intervals through the ultrasound prostate imaging phantom. The ultrasound prostate phantom is available from Computerized Imaging Reference Systems Inc. and contains a model of a prostate, urethra, and seminal vesicles immersed in a gel filled plastic box. The box has a cylindrical hole in the base for the insertion and positioning of the transrectal probe and a perineal membrane for performing practice brachytherapy implants. FIGS. 4A and 4B display a schematic of the brachytherapy phantom. Once the static image slices have been digitized they were then inputted to the software in a continuous cycle to model actual real time acquisition of a full volume. Multiple sets of image slices can be obtained and randomly cycled to more accurately simulate the actual three-dimensional real time ultrasound probe 12. The image slices are input to the software transparently.

Figure 13B:
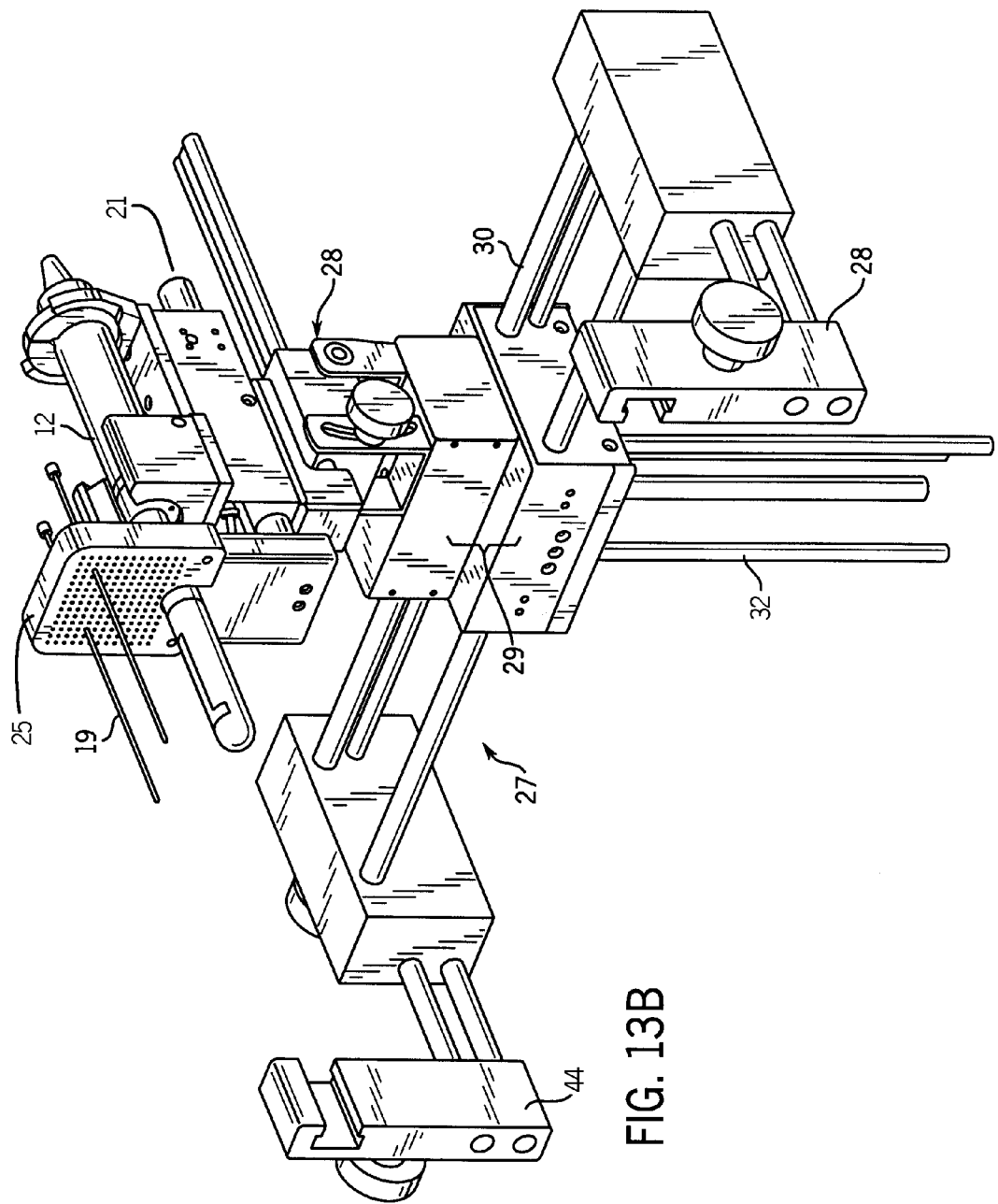

A probe stabilization system 27 (see FIG. 13B) is designed for use with any standard probe holder/stepper 21, yet it is optimized for use as part of the system 10. This stabilization system 27 attaches easily and quickly to the cysto or operating room table using clamps 28, yet provides maximum flexibility during patient setup. The stabilization system 27 provides for five degrees of freedom of motion, yet is robust and stable. The probe stabilization system 27 includes a stepper probe stand control 44 which allows up and down movement. Further motion control is provided by stabilizer control 29 which enables up and down motion and left to right along rods 30 (horizontal) and rods 32 (vertical). Gross motions are positively controlled in a stable manner. Fine motions are obtained with the same controls and are exactly reproducible.

A variety of the templates 25 (see FIG. 2) for the needles 19 can be used with the system 10. All of these implant templates are disposable preferably. The system 10 can also accommodate use of other standard templates 25. The system software (see the Computer Program Listing Appendix) can store the configuration of any number of the templates 25 for immediate recall. Each template 25 stored in the system 10 is spatially registered with each ultrasound system configuration stored in the system software.

The system templates 25 provide assurance of sterility for patient contact at a cost similar to that of sterilization of the usual standard templates. The disposable system templates 25 are a fraction of the cost of standard reusable templates and provide greater safety.

There are several possible image processing cards which could be utilized; however, using current modalities each of the processing cards is configured specifically for three-dimensional. The three-dimensional image raster is buffered; and thus, for example, if the two-dimensional images are 512×512 and there are sixteen image planes in the probe 12, and each pixel is a byte (256 gray scales), at least a 512×512×16 byte=4.2 Mbyte image buffer in the card 14 is needed. Several commercial cards (for example, made by Coreco, Matrox and Integral Technologies) can be equipped with this amount of video RAM (VRAM), but the way the card's hardware interacts with the computer's video and software drivers does not utilize this data in three-dimensional. Current available methodologies enable augmenting the software and some hardware of these cards so that they can act as a three-dimensional card. The processing and memory architecture preferably is designed to allow for simultaneous image acquisition and processing. The digitizing card should also preferably have standard imaging tools, such as real time window and leveling, zoom and pan of the ultrasound images. Some existing cards (e.g., Matrox; Coreco) do provide standard imaging tools.

The three-dimensional image data arising from the ultrasound probe 12 is preferably buffered on the imaging card 14. The three-dimensional image is preferably represented as a series of two-dimensional images. This is referred to as the image stack or three-dimensional image raster. The three-dimensional image raster is represented in memory as a linear array of bytes of length N×M×P where N is the width of the two-dimensional image in pixels, M is the height a two-dimensional image in pixels, and P is the number of two-dimensional images in the image stack.

In a preferred embodiment the user can include defined formats. Entire three-dimensional image stacks at specific times during the intraoperative session can be stored in the DICOM standard. The user will have the ability to select a three-dimensional image volume for archiving as part of the system software. These image stacks can then be reviewed in any of the various visualization modes (standard orthogonal two-dimensional views, oblique two-dimensional views, or three-dimensional translucent views) as described above. In addition, the user will have the ability to store any of the two-dimensional views available at any time during the intraoperative session.

The computational platform can, for example, be any form of computing means, such as the personal computer 16, which incorporates a PCI bus architecture. Currently, PCI bus is preferable over the ISA or EISA bus because the PCI bus is much faster. However, a generic system which will be suitable for this applicable will be described. A 200 MHz (or greater speed) Pentium/Pentium-Pro computer supplied with 128 Mbytes of RAM and a 6.0 Gbyte hard disk should be sufficient RAM and disk memory to run the software in a real-time fashion and to archive all patient data. There should be sufficient RAM to facilitate host image processing in parallel with onboard image processing for quality assurance checks. A high resolution monitor capable of displaying at least 1280×1024×64 bit resolutions is preferably used.

Based on currently available technology, the ultrasound images obtained from the ultrasound imaging system of the ultrasound probe 12 can be of good diagnostic quality. When transforming this input image data into a three-dimensional representation, whether in the three-dimensional perspective mode or the real time VR mode, the resultant volumes can, however, be noisy and hinder diagnostic and spatial accuracy. In order to improve the image quality, a number of conventional hardware and software filters can be used which will filter the incoming image data stored on the imaging card 14. Routines such as image pixel averaging, smoothing, and interpolation can improve the three-dimensional rendering of the imaging volume. These sets of filters or routines are to be distinguished from the set of standard imaging tools running on the host CPU which are available within a conventional imaging software package.

Figure 6:
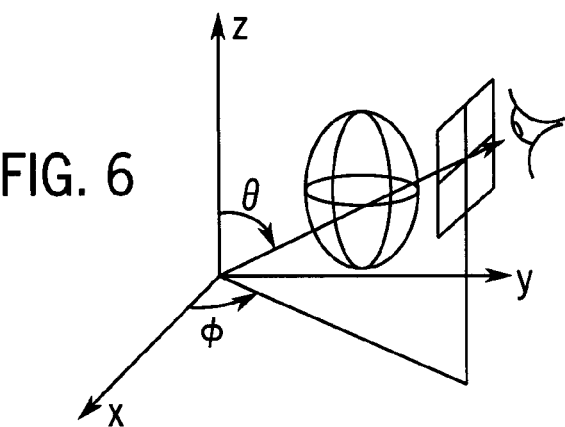
FIG. 6 illustrates the viewing geometry for a three-dimensional translucent reconstruction of an image.
Figure 5A:
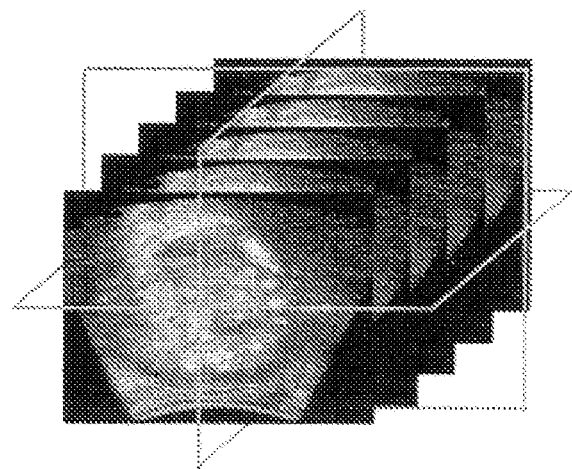
FIG. 5A illustrates reconstruction of standard orthogonal image planes from a three-dimensional image stack and FIG. 5B the reconstruction of oblique image planes from a three-dimensional image stack.
Figure 5B:
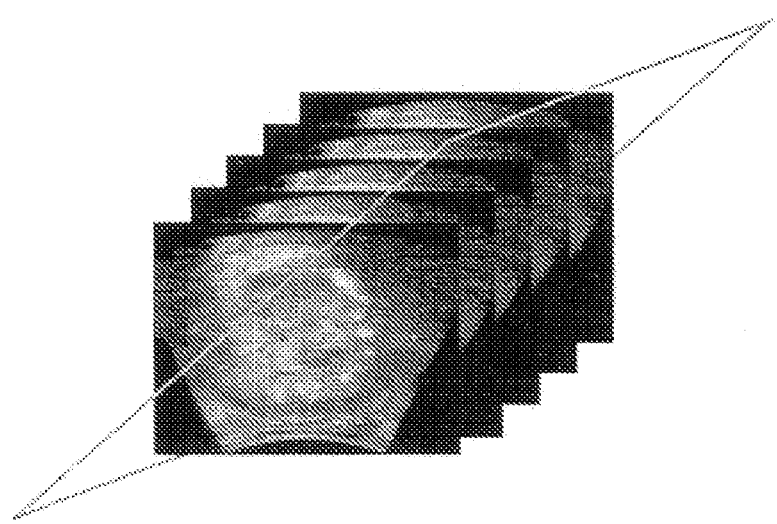
Figure 7A:
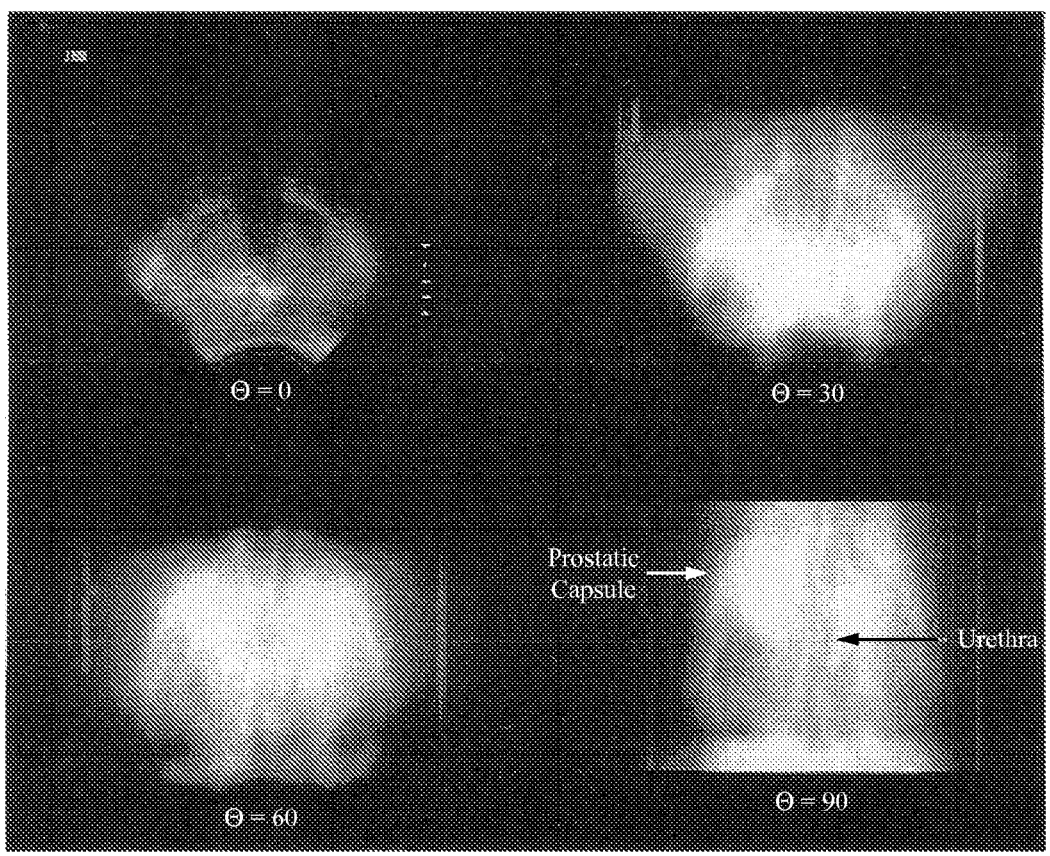
FIG. 7A illustrates translucent images of a human prostate for four different viewing angles and FIG. 7B illustrates translucent images of a phantom organ for six different viewing angles.
Figure 7B:
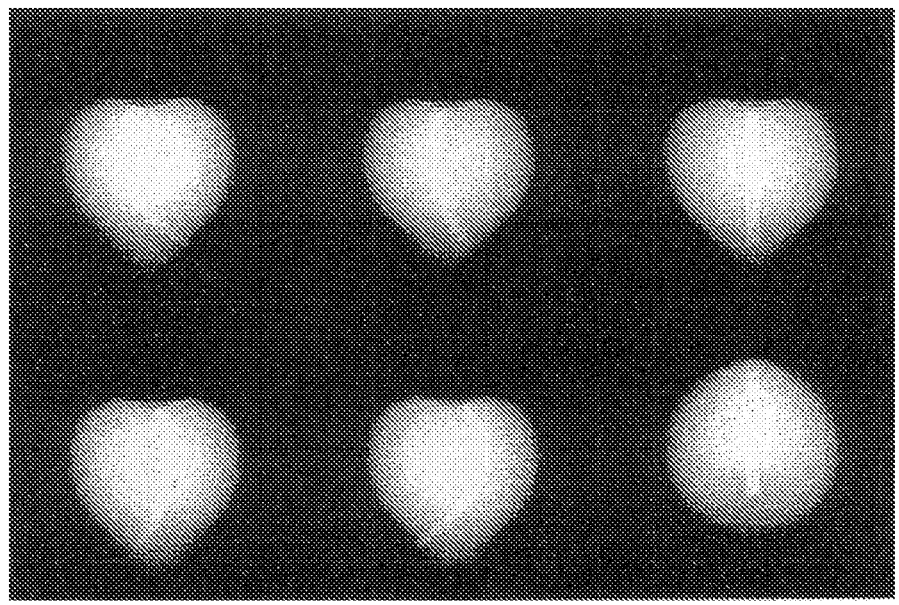

In the preferred embodiment, three of the perspective views are the standard transverse, coronal and sagittal two-dimensional views. These three orthogonal views are taken from a user specified location within the imaging space. For example, the user can request that the three orthogonal views have their common centers at a spatial position of (5.0 cm, 15.0, 25.0 cm) relative to the origin of the template system. One also can select the reference point of either of the three orthogonal views independently, that is the three views do not have to have common center points. As mentioned hereinbefore, FIGS. 5A and 5B show examples of several example two-dimensional views from a three-dimensional ultrasound image volume. FIG. 6 shows a number of possible viewing directions, and FIGS. 7A and 7B give further examples of translucent three-dimensional viewing from different angles. The three-dimensional ultrasound image volume was obtained from actual ultrasound images of a human prostate and of a prostate implant phantom.

On each of the views, one can define, draw and edit contours using conventional computer software, such as Microsoft Foundation Class (MFC) view files. Each contour can be given a unique name by the user, and then drawn by the user using the mouse of the computer 16. All attributes of the contours such as name and color can, based on conventional imaging software, be user selectable. The user can also edit the contours by selecting functions, such as adding a point to a contour, deleting a point from a contour or deleting the entire contour. Once the contours are defined, the user has the option to render them in three-dimensional or view in conventional two-dimensional mode on the three-dimensional perspective mode or viewed in the VR mode. Again, all contour three-dimensional attributes such as color, lighting, and shading are user controlled. The contours by default appear on the two-dimensional images, however, the user can control the individual contour's two-dimensional and three-dimensional visibility.

Figure 8:
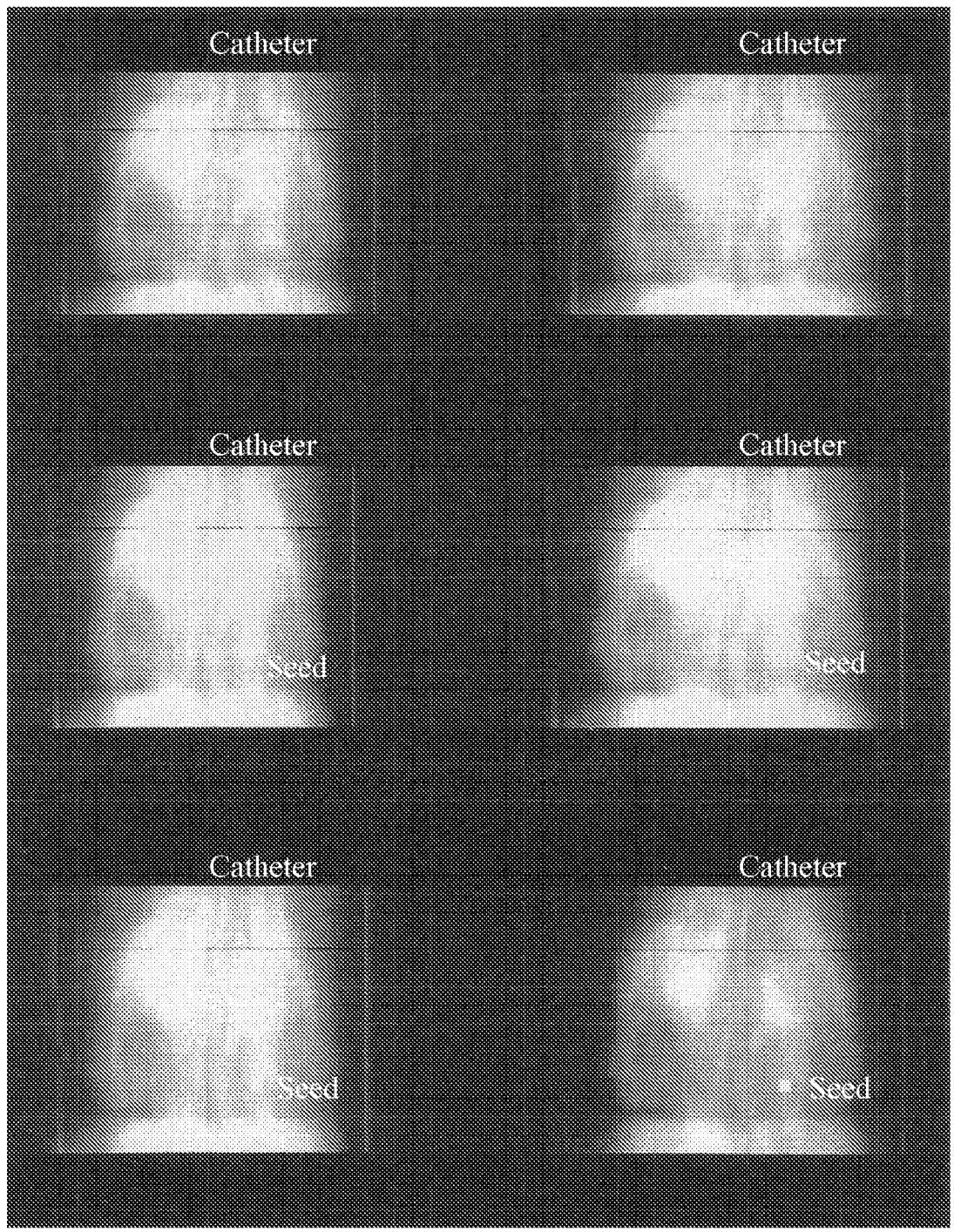
FIG. 8 illustrates a time sequenced image of the prostate organ in FIG. 7A showing approach of a catheter containing a radioactive seed, deposition of the seed and withdrawal of the catheter leaving the seed.

In order to improve the ability to visualize the real time, three-dimensional information, the three-dimensional image raster can be rendered as a real time, transparent, three-dimensional volume. This transparent volume can be viewed and displayed on the monitor of the computer 16 at any arbitrary viewing angle and is calculated using conventional three-dimensional object reconstruction algorithms. Such standard algorithms can render a large imaging volume in fractions of a second, even on present day computing platforms. The transparent nature of the reconstruction thus allows the user to "see" inside any objects which appear in the imaging volume. For example, if the prostate is imaged in the imaging volume, then it will be reconstructed as a transparent volume, in which other anatomical landmarks such as the urethra, tissue abnormalities or calcifications can be seen. In addition, if any other objects such as needles or catheters are inserted into the prostate, and if they are visible in the ultrasound images, they will be seen as they enter the prostate (see FIG. 8 showing introduction of the seed 18 with the catheter/needle 19). Since the volumes are rendered as transparent solids, the needles 19 (and other articles) can thus easily be seen as they move inside the prostate volume as well. Since the ultrasound images are obtained in real time, the three-dimensional perspective reconstruction is also rendered in real time. The preferred algorithm for the perspective three-dimensional reconstruction is the known Bresenham ray-trace algorithm.

As described above, in the routine process of brachytherapy planning, the patient undergoes an initial volumetric ultrasound scan using the probe 12. This scan is done before the radiation therapy planning or the actual implant. During the radiation therapy planning, the ideal positions of the radioactive seeds 18 (see FIG. 1A) within the prostate are determined. This ideal seed distribution is optimized to deliver a dose distribution within the prostate that will deliver all the radiation dose to the target volume only, while sparing the surrounding healthy tissues such as the rectum and bladder. The optimal positions of the seeds 18 and the optimal position of the needles 19 are recorded for later use in the operating room when the needles 19 are loaded into the patient. The seeds 18 are then loaded into the needles 19, and the physician then attempts to place the needles 19 inside the prostate using a template 25 according to the treatment dose plan positions (again, see example in FIG. 8)

Figure 14:
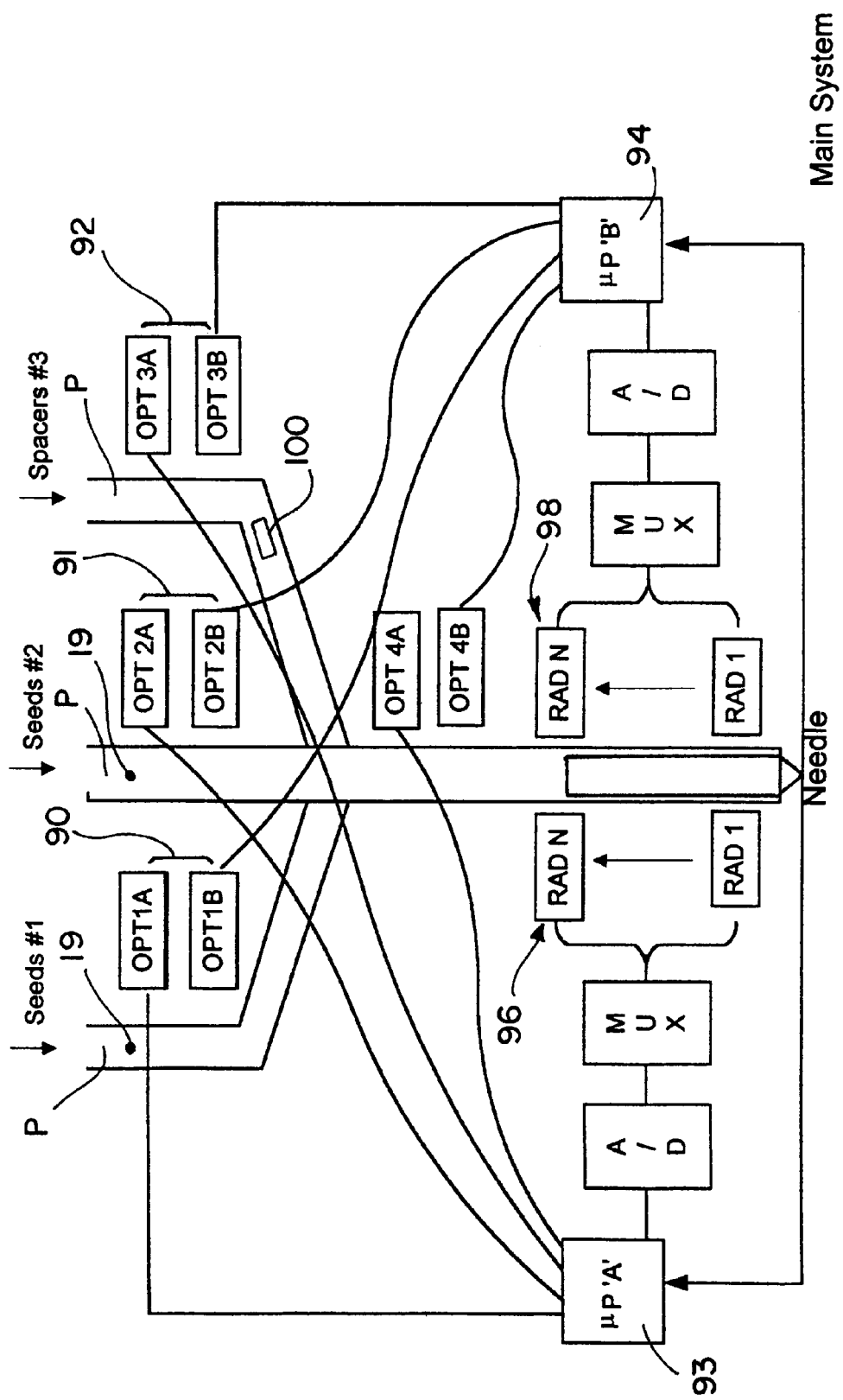
FIG. 14 illustrates a redundant monitoring and automatic loading system for radioactive seeds and inert spacers.

In the most preferred embodiment the seeds 18 are loaded through the needles 19. A selection of different types of the seeds 18 (different levels of radioactivity) can be loaded through passageways, P, shown in FIG. 14. Optical sensors 90 and 91 are redundantly disposed adjacent each of the passageways P with an associated microprocessor 93 and 94 monitoring the number of the seeds 18 being instilled through the needle 19. Radiation sensors 96 and 98 monitor the radiation activity of the seeds 18 being loaded into the needle 19. Spacers 100 are also instilled into the needle 19 for separating the seeds 18 to achieve the desired level of radiation activity and radiation contours. Optical sensors 92 sense, redundantly as for the seeds 18, the passage of the spacers 100. Furthermore, optical sensors OPT4A and OPT4B, as shown in FIG. 14, are positioned downstream from where the three passageways P merge to form a single passageway. Thus, optical sensors OPT4A and OPT4B are positioned to sense redundantly the instillation of both seeds and spacers through the needle.

In a most preferred form of the invention, an automatic seed/needle loading method is implemented automatically loading implant needles 19 with the radiation seeds 18 and spacers 100 based upon a pre-plan (dose plan) determined in the operating room (OR). This method accommodates the spacers 100 and separate leaded-acrylic see-through "bins" for the seeds 18 of two different activity levels. Thus, the needles 19 can be auto-loaded based upon optimal dose plans requiring seeds of different activity levels. The automatic seed/needle loading method and system interfaces directly to the computer 16 and reads the dose plan information using the software of the Computer Program Listing Appendix. A display on the auto-loader then displays to the operator each needle number, template coordinate location, and status of needle loading. Each of the needles 19 are attached one at a time to the auto-loader assembly with a standard luer lock. The auto-loader has a sensor at the needle attachment point which detects if the needle 19 is attached for loading. Each of the needles 19 are then loaded in accordance with the pre-plan.

The automatic seed/needle loading method and system is therefore completely double-redundant, as mentioned hereinbefore. It incorporates the use of two totally independent microprocessors 93 and 94 which constantly check each other. Both the microprocessors 93 and 94 are also in communication with the system computer 16. The seeds 18 and the spacers 100 are optically counted independently. Needle loading is optically checked for total number of loaded items and, further, a radiation detector array scans each needles 19 to confirm that the seed/spacer loading radiation pattern matches the pre-plan. This automatic method and system will do so in the operating room in minimal time, without the risk of human error in the loading of needles. The seed loading method will include a pair of redundant 8051 microcontrollers (the microprocessors 93 and 94) which will be interfaced to the dose-planning and implant system computer 16 via a serial port. This interface will read the dose pre-plan information from the computer 16, without the need for paper printouts and manual loading. That information will be transferred to a controller which controls the loading of each needle 19. The requirements and design criteria for the automatic seed-needle loading method and system are described as follows: self-contained and capable of loading seeds and spacers; system will protect operator of system from radiation; dual redundant counting of seeds and spacers; dual redundant radiation detectors for measuring radiation from active seeds versus spacers; dual redundant measurement of radiation seed positions in needles; system check for failure of either or both redundant counting and measurement systems; alarm to both operator and to dose-planning and implant computer system in the event of error; ongoing account of seed and spacer inventory; tracks needle loading configuration and displays to operator the designated template grid hole coordinates for each needle loaded; sterilized cassettes for holding seeds and spacers, plus sterilizable needle connector; includes one cassette for seeds and one cassette for spacers; dispenses one seed and one spacer at a time, and verifies optically and by radiation detector; system displays needle number and template grid location during loading procedure; automatic acquisition of needle loading plan from main system computer; serial interface with handshake protocol and verification; self-contained (mechanical, power, logic, microcontrollers); operates only if connected to main system computer.

A convenient storage system for the needles 18 can be loaded by the automatic seed/needle loading method system. The face of this unit has a hole grid pattern which matches the implant template 25. Loaded needles may be inserted into this unit until they are used. The entire unit is shielded for radiation leakage minimization. The template-like face of the unit is available in both a reusable, sterilizable version and disposable versions which match all standard implant template faces. Faces of the unit detach easily and quickly for sterilization or disposal.

Figure 9:
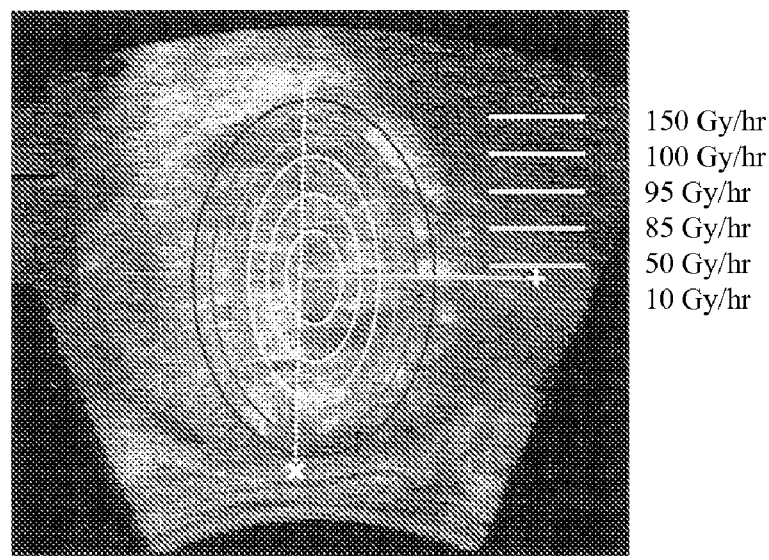
FIG. 9 illustrates isodose distributions of radiation from a single radioactive seed.

The dose as a function of position for a cylindrical $^{125}$I seed of a given activity can be determined from a lookup table or calculated from a conventional analytic formula. The dose field can be visualized as a set of isodose lines in two-dimensional or isodose surface in three-dimensional (see FIG. 9). The dose computation routine is based upon the TG43 standard adopted by the AAPM (American Association of Physicists in Medicine) entitled "Dosimetry of Interstitial Brachytherapy Sources": Recommendations of the AAPM Radiation Therapy Committee Task Group No. 43 which specifies the dose model and the data used in the dose calculation. This particular implementation runs extremely fast on a conventional 233 MHz PC, computing the dose for a single seed in less than 0.5 seconds. The total three-dimensional dose distribution within the prostate for a 100 seed implant requires only 50 seconds, or less than one minute total computation time. Thus, this can be done "on line" in the operating room.

In the two-dimensional, three-dimensional perspective, or the real time VR modes, the user has the ability to view the optimized seeds 18 and the needles 19 in the same volume as the real time ultrasound data. This allows the physician to see exactly where the needles 19 should go and hence make adjustments to position the needles 19 optimally. The pre-planned, optimal positioned needles 19 and the seeds 18 can be rendered again as a transparent solid, the color of which is user selectable. As the real needles 19 are inserted into the prostate, their positions relative to the ideal needle placements based on the dose plan can be monitored in real time. Any deviation of the position of a given needles 19 can be quickly and accurately readjusted so as to follow the path of the ideal needles 19. As the different needles 19 are placed at different positions inside the prostate, the viewing angle can be adjusted to facilitate viewing of the needle or catheter placement. FIGS. 5A and 5B displays perspective three-dimensional views and the three orthogonal reconstructions of the image data along with the pre-planned catheter positions. The pre-planned needles 19 can also be viewed in the VR mode as virtual objects overlaid onto the imaging volume.

Figure 10:
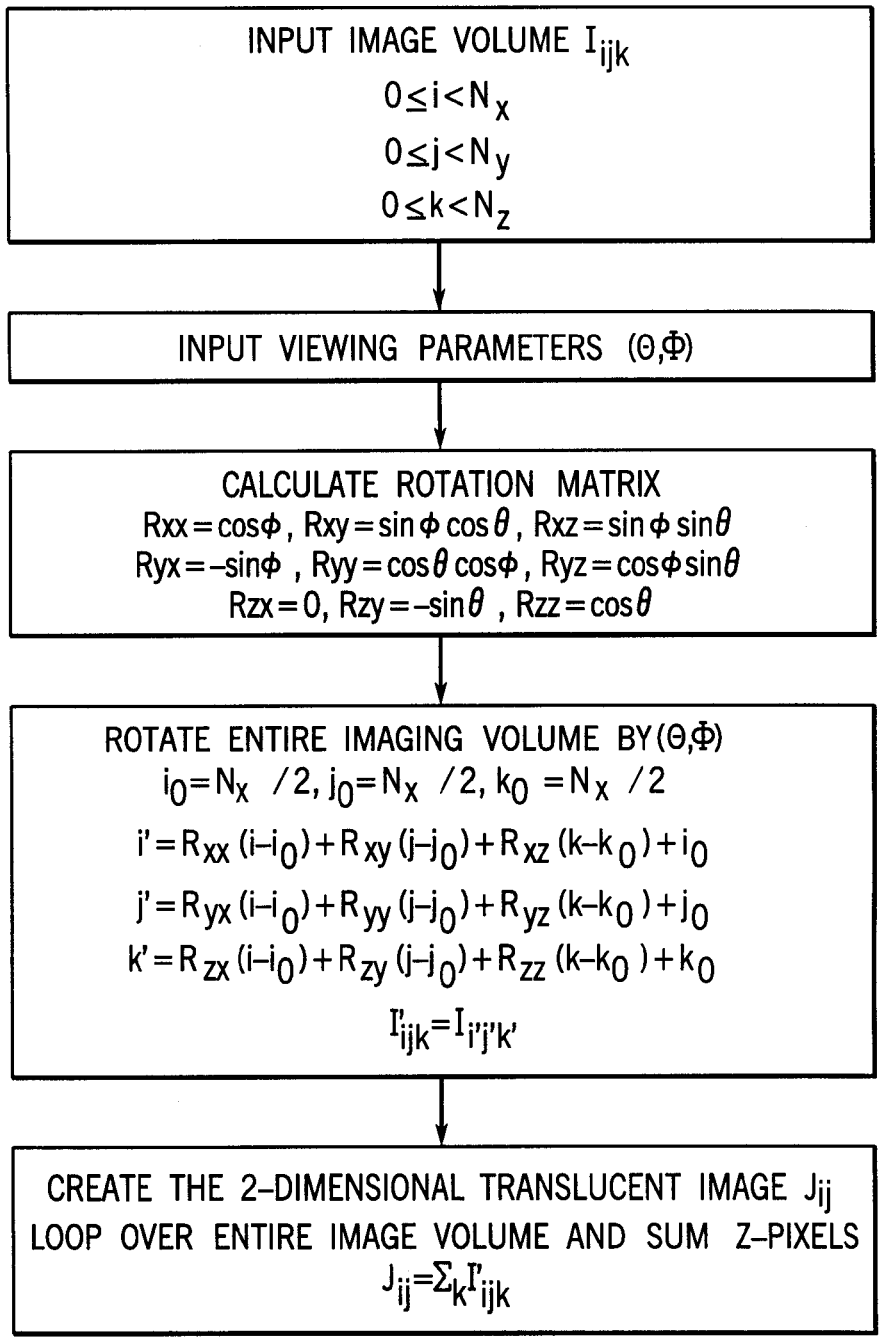
FIG. 10 illustrates a flow chart of software routine for processing imaging data for visualization.
Figure 12A:
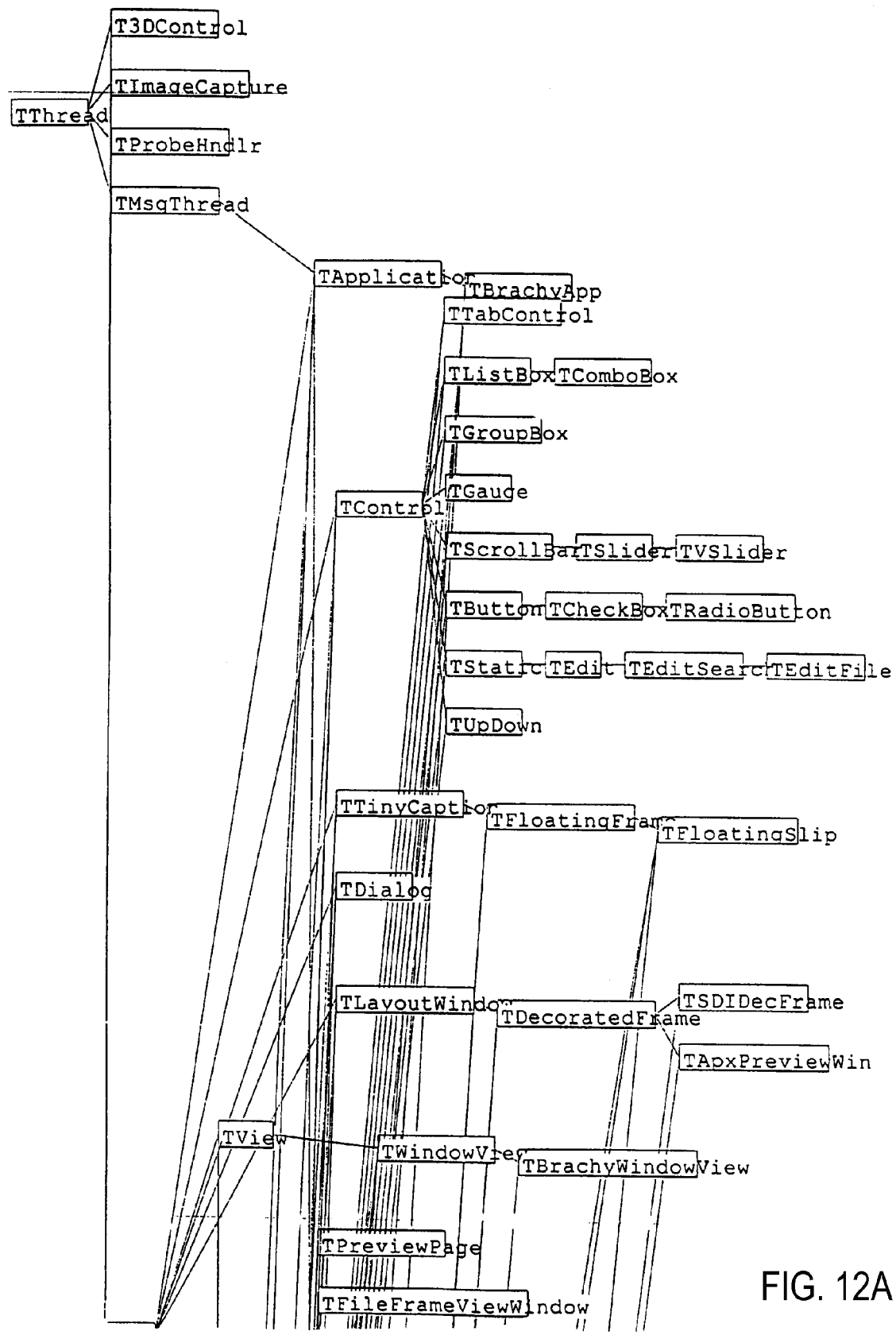
Figure 12B:
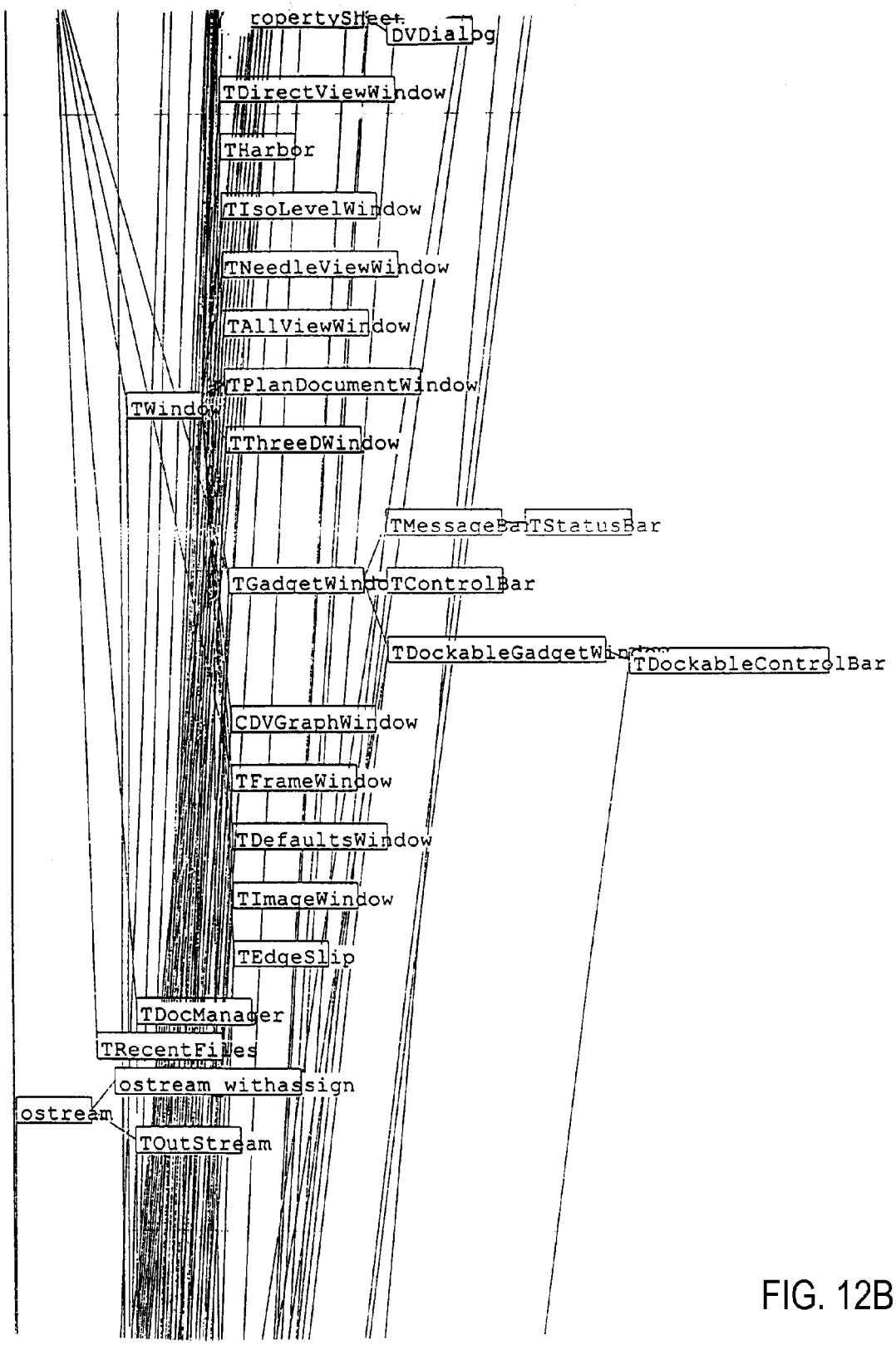
Figure 12C:
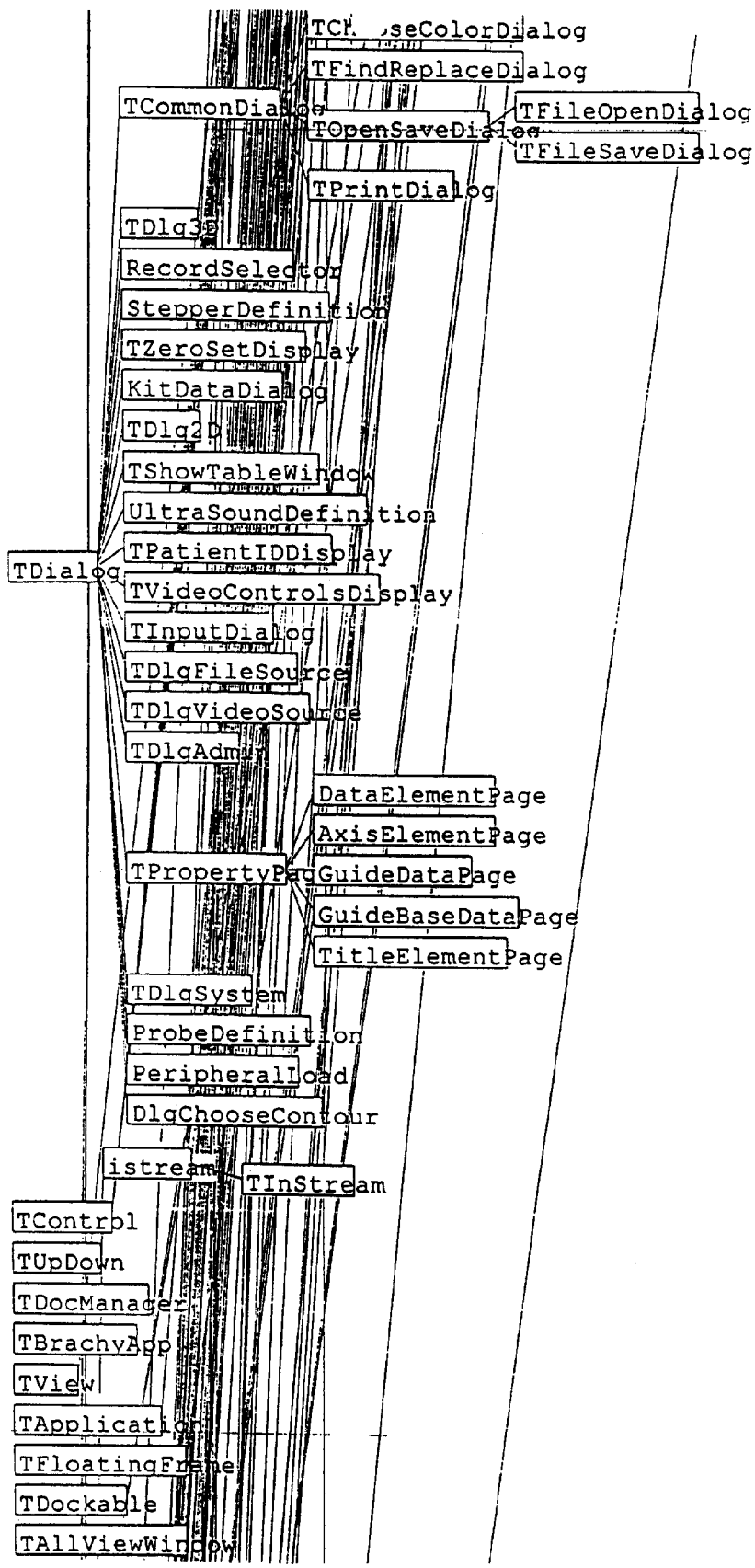
Figure 12D:
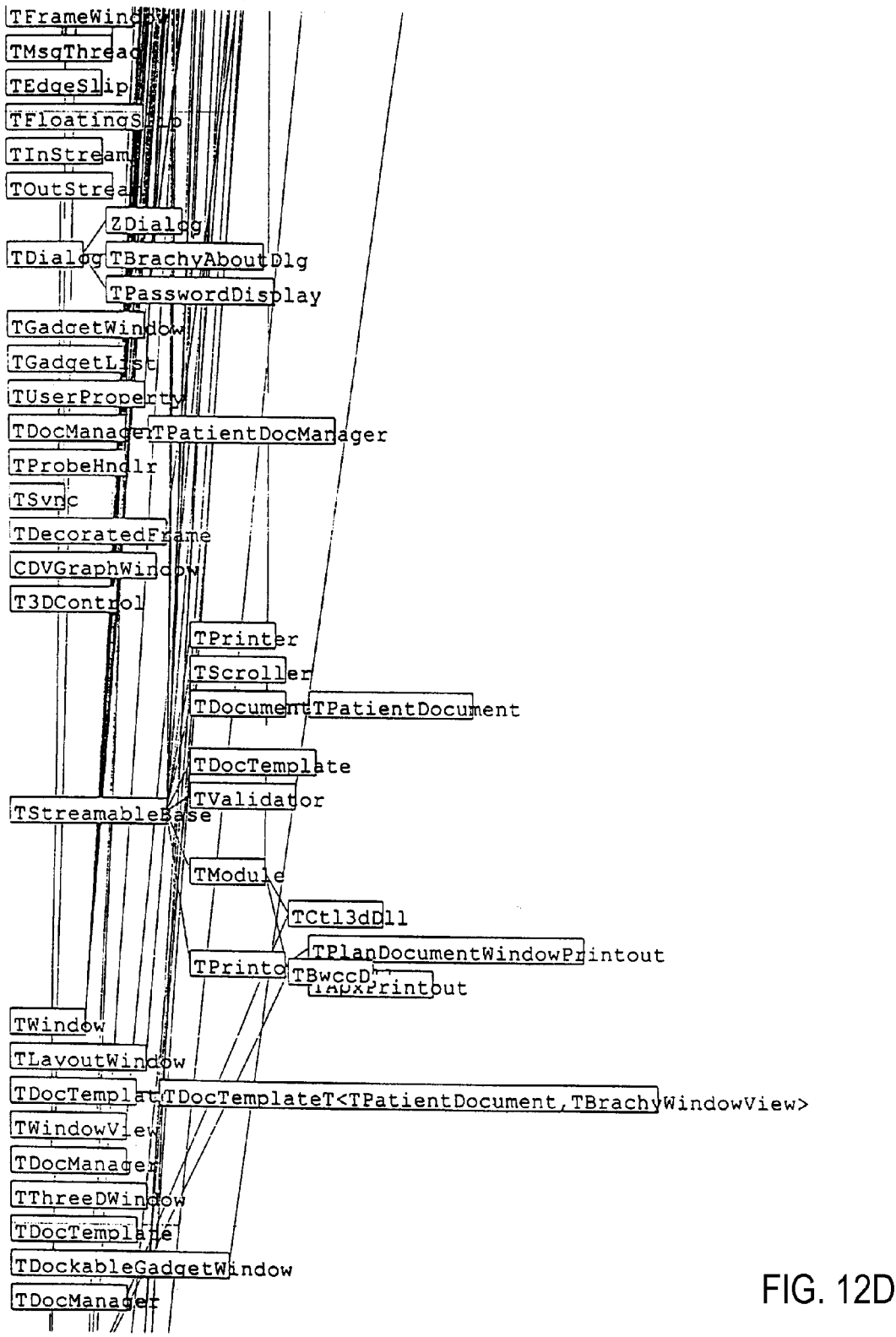
Figure 12E:
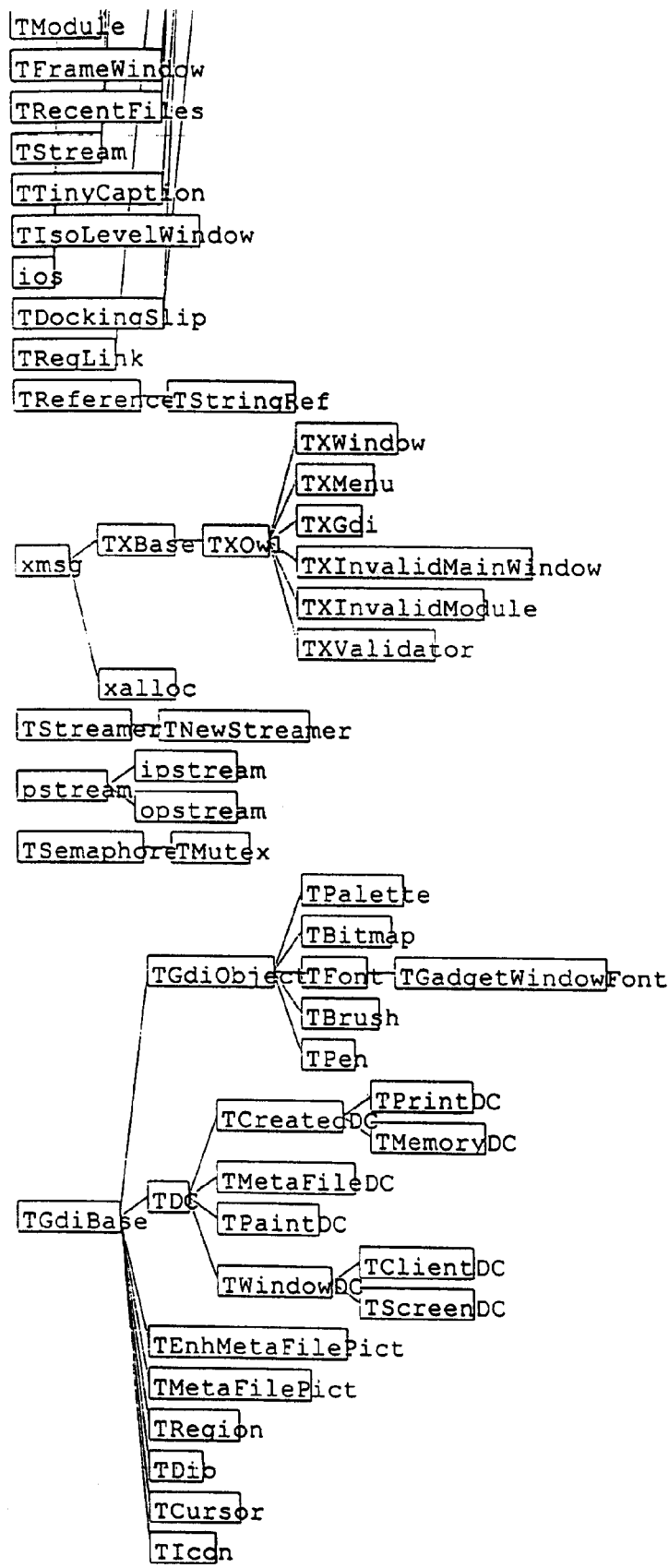
Figure 12F:
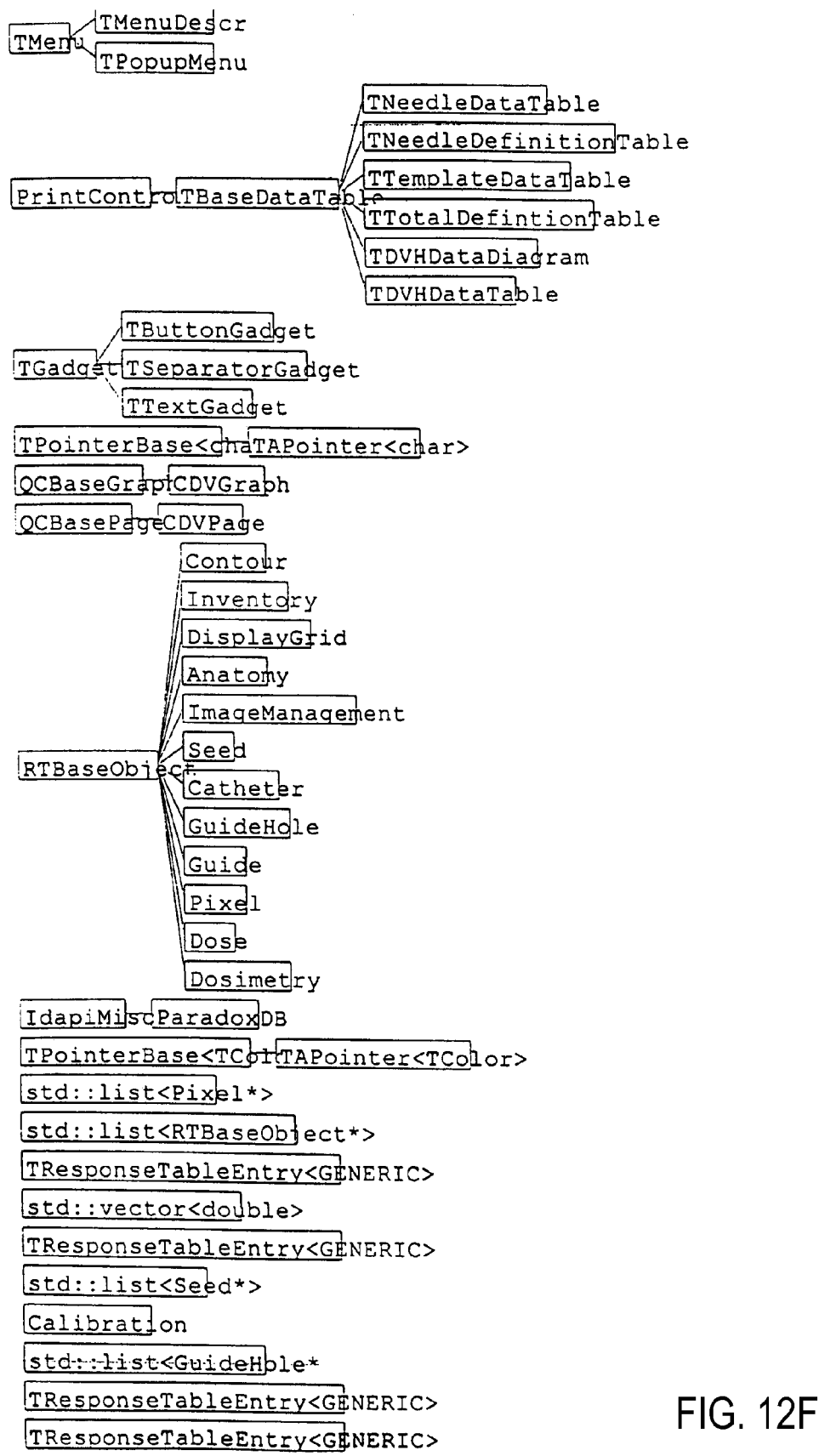

A flowchart description of the translucent volume visualization methodology is shown in FIG. 10. The input image volume is described by the vectors i, j, k of appropriate magnitude for the volume. The viewing angle parameters are the angles θ, Ø described on FIG. 6 and FIG. 10. The rotation matrix, R, is calculated using the formulae given in the flowchart of FIG. 10. The entire imaging volume is calculated by multiplying the rotation matrices in the x, y, z directions by the respective vectors i, j and k describing the incremental portions along the x, y, z directions. Thus, the multiplying vector is $(i-i_o, j-j_o, k-k_o)$ where $i_o, j_o, k_o$ are the starting points along x, y and z axes and the volume is determined by summing the component contributions shown in FIG. 10. The three-dimensional translucent image is then created by computing the translucent two-dimensional image over the entire image volume and summing the z-pixels.

Figure 11:
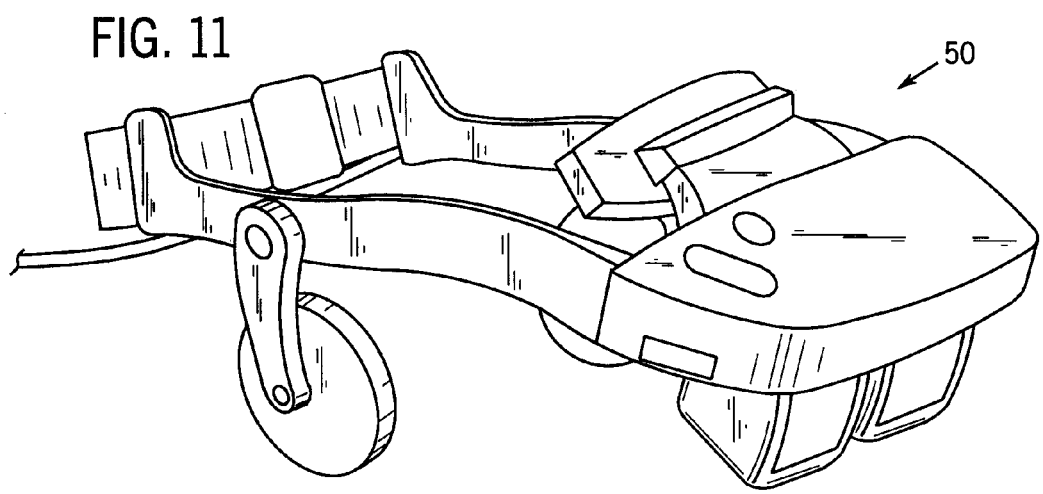
FIG. 11 illustrates a virtual reality head mounted display.

A virtual reality interface system can be composed of a conventional head mounted display (HMD) 50 shown in FIG. 11 and a 6D (x,y,z, roll, pitch, yaw) tracking system. The HMD 50 consists of two color monitors which mount to a head set in the position directly in front of the eyes. The HMD 50 is based on the principal that whatever is displayed on each monitor is directly incident on the retina for each eye, and hence true three-dimensional images can be created by rendering objects as three-dimensional perspective images for each eye. Given the distance between the eyes (the interocular distance which is approximately 80 mm) and the distance and spherical angles of the distance of the center line between the eyes from the coordinate origin, the two-dimensional images which appear in each of the two monitors can be determined exactly as described above. This results in a true three-dimensional image as perceived by the user. Therefore, as the user moves his or her head or moves around the room, the distance from the origin and the spherical angles also change. This motion of the user or user's head can be obtained from the VR tracking system. Given these spatial parameters, the images which are reconstructed in the two eye monitors can be updated in real time, giving the user the illusion of the object really existing in three-dimensional space. The user literally has the ability to walk around the object, viewing it in three-dimensional space.

Instead of reconstructing computer generated geometric objects as is usually the case in VR, the transparent, three-dimensional reconstruction of the real time imaging data will preferably be reconstructed. Hence as the physician walks around the patient undergoing the implant, the physician will see the three-dimensional ultrasound volume mapped inside the patient's pelvis, spatially correlated to the position of the patient's real prostate (or other organ) and anatomy. The physician can "see" inside the patient to the extent of what is visible in the ultrasound imaging volume. Since the ultrasound probe 12 is locked down to the template, which is then secured to the floor, the exact positions of all voxels in the ultrasound imaging volume are known exactly relative to the template, and hence relative to the room.

As the needles 19 are inserted into the patient, they will appear in the image volume and hence are reconstructed in the VR reconstruction. All of this occurs in real time so that the physician also can see the needles 19 enter the prostate in real time. As mentioned above, if the pre-planned, optimized needles 19 are displayed, the physician can then see the position of the actual needles 19 as they are being inserted relative to the optimal placement. Hence, the physician has the ability to adjust the needles 19 to correspond to their optimal positions. In addition, since the needles 19 are automatically extracted, the computer software has the ability to calculate and render the three-dimensional dose distribution in real time as the needles 19 are being inserted.

As an example, a currently available, a fast and inexpensive HMD is made by Virtual-IO Corporation (Mountain View, Calif.). The HMD is full color with two 0.70 LCD displays with a resolution of 180,000 pixels per LCD panel. The video input is NTSC with field sequential format. The LCD panels are semitransparent, allowing the real outside world to be included in the virtual reconstruction. The field of view is 30° for each eye. A six degree of freedom (6 DOF) tracking system can also be attached to the HMD. The 6 DOF tracking system allows for the determination of the spatial position of the user's head and the yaw, pitch, and roll of the head. The conventional head set weighs only 8 ounces and comes with stereo sound. Stereo sound is an extremely valuable technology in the operating room. With this capability, the physician has the ability to monitor the patient's heart rate and respiration rate while performing the implant. Hence any fluctuation in the patient's vital signs can be instantly accessed and acted thereon if necessary.

The radioactive seeds 18 are made of high density material such as stainless steel, and hence have a very bright response in the ultrasound images. Therefore, automatic seed detection in the ultrasound images can readily be accomplished, for example, by a simple thresholding algorithm along with the requirement that the resultant objects which are removed by threshold have a certain maximum size determined by the actual size of the seeds.

Near-real-time visualization will provide immediate feedback to the physician during the implant process itself. There is a clear need for the visualization being available during the implant process. The nearly real time visualization is of great importance to the effective use of a translucent overlay of the ideal seed pre-plan (from the therapy planning process) in the three-dimensional volume. The physician can "see" in nearly real time the relationship of the needles and seeds being implanted to the ideal pre-plan locations and quickly accommodate redirection required prior to leaving the radiation seeds. Further, the need for this in three-dimensional representation is very important to overcome the greatest fundamental limitation in brachytherapy, which is knowing at the same time both the lateral placement and longitudinal placement of needles and seeds relative to the target volume and pre-plan. This is a three-dimensional problem which has up until now been addressed in two-dimensional in a stepwise fashion without the ability to "see" the exact location of where you are in the target. This real time three-dimensional visualization also would speed the implant process in the case of brachytherapy as well as make it more accurate. It would also speed other minimally invasive surgical procedures and localized tissue ablation procedures (for example, cryosurgery or localized selected ablation of diseased liver tissue or local removal of breast tissue). These procedures could be accomplished with real time visualization inside the tissue being treated with greater accuracy in shorter time. This aspect would reduce operating room time and costs to the patient and health care system.

While preferred embodiments of the inventions have been shown and described, it will be clear to those skilled in the art that various changes and modifications can be made without departing from the invention in its broader aspects as set forth in the claims provided hereinafter.

What is claimed is:

1. A system for monitoring loading of radiation into an insertion device for use in a radiation therapy treatment to determine whether the treatment will be in agreement with a radiation therapy plan, the system comprising:
   at least one radioactive source for providing radiation therapy to a treatment region of the patient;
   an insertion device, the insertion device being configured to hold the at least one radioactive source, the insertion device for insertion into the treatment region to provide therapy to the treatment region of the patient via the at least one radioactive source held thereby;
   a computer automated optical sensor that is positioned to automatically sense loading of the at least one radioactive source into the insertion device and generate optical sensor output data indicative thereof;
   a radiation sensor that is positioned to sense a radiation pattern of the at least one radioactive source loaded in the insertion device and generate radiation sensor output data indicative thereof; and
   a processor in communication with the computer automated optical sensor and the radiation sensor, the processor being configured to (1) interface with an external device to receive data representative of the radiation therapy plan, the plan data defining (a) a number of radioactive sources to be loaded into the insertion device and (b) a radiation pattern for the planned treatment, (2) process the optical sensor output data to determine a quantity of radioactive sources that are currently present in the insertion device, (3) process the radiation sensor output data to determine an actual radiation pattern emitted by the at least one radioactive source held by the insertion device, and (4) compare the determined quantity and the determined actual radiation pattern with the plan data to thereby determine whether the actual treatment agrees with the therapy plan.

2. The system as defined in claim 1 wherein the insertion device comprises at least one selected from the group consisting of a needle and a catheter.

3. The system as defined in claim 1 wherein a plurality of radioactive sources are loaded into and held by the insertion device, the system further including:
at least one spacer for placement adjacent at least some of the radioactive sources within the insertion device,
a first container for holding at least one of said plurality of the radioactive sources;
a second container for holding the at least one spacer; and
another computer automated optical sensor that is positioned to automatically sense loading of at least one spacer into the insertion device and generate another optical sensor output data indicative thereof; and
wherein the radiation therapy plan further defines a number of spacers to be loaded into the insertion device, and wherein the processor is further configured to process the another optical sensor output data to determine a quantity of spacers to be loaded into the insertion device and compare the determined spacer quantity with the plan data to thereby determine whether the actual treatment agrees with the therapy plan.

4. The system of claim 3 wherein the plurality of radioactive sources comprise radioactive sources of at least two different levels of radioactivity.

5. The system of claim 4 wherein the first container comprises at least a first bin and a second bin, each bin for holding radioactive sources of different radioactivity levels.

6. The system of claim 3 further comprising:
a controller in communication with the processor; and
an auto-loader in communication with the controller, wherein the auto-loader is configured to automatically load the radioactive sources and the at least one spacer into the insertion device under command of the controller; and
wherein the controller is configured to receive plan data from the processor and provide commands to the auto-loader to perform automatic loading of the radioactive sources and the at least one spacer in accordance with the plan data.

7. The system as defined in claim 6 further comprising a template having a plurality of openings for receiving the insertion device during the treatment, each opening corresponding to a template coordinate location.

8. The system of claim 7 wherein the therapy plan comprises a plurality of insertion devices to be placed into different template openings, the plan data further defining, for each of the insertion devices, (1) a number of radioactive sources to be loaded into that insertion device, (2) a number of spacers to be loaded into that insertion device, (3) a radiation pattern for that insertion device, and (4) a template coordinate location for that insertion device, and wherein the auto-loader is further configured to automatically load the radioactive sources and the at least one spacer into the plurality of insertion devices under command of the controller, and wherein the auto-loader further comprises a display, the display being configured to display to the user the template coordinate location that corresponds to the insertion device being loaded and a status for loading each insertion device as the insertion devices are being loaded.

9. The system of claim 8 wherein the plan data further defines an identifier for each insertion device, and wherein the auto-loader display is further configured to display to the user the identifier for the insertion device as that insertion device is being loaded.

10. The system of claim 9 further comprising an alarm for notifying the user if the processor determines that the actual treatment does not agree with the therapy plan.

11. The system of claim 8 wherein the auto-loader is further configured to load radioactive sources and spacers into the insertion devices one at a time.

12. The system as defined in claim 1 wherein the processor is further configured to compare the determined quantity and the determined actual radiation pattern with the plan data to thereby determine whether the actual treatment agrees with the therapy plan before the insertion device is actually inserted into the treatment region of the patient.

13. The system of claim 12 wherein the processor comprises a plurality of redundant microprocessors.

14. The system of claim 13 wherein the optical sensor comprises a plurality of redundant optical sensors.

15. The system of claim 14 wherein the radiation sensor comprises a plurality of redundant radiation sensors.

16. The system of claim 13 wherein the radiation sensor comprises a plurality of redundant radiation sensors.

17. The system of claim 12 wherein the optical sensor comprises a plurality of redundant optical sensors.

18. The system of claim 12 wherein the radiation sensor comprises a plurality of redundant radiation sensors.

19. The system as defined in claim 1 wherein a plurality of radioactive sources are loaded into and held by the insertion device, the system further including:
at least one spacer for placement adjacent at least some of the radioactive sources within the insertion device;
a first container for holding at least one of said plurality of the radioactive sources;
a second container for holding the at least one spacer; and
wherein the optical sensor is further configured to sense loading of the at least one spacer into the insertion device, wherein the radiation therapy plan further defines a number of spacers to be loaded into the insertion device, and wherein the processor is further configured to process the optical sensor output data to determine a quantity of radioactive sources and spacers to be loaded into the insertion device and compare the determined quantity with the plan data to thereby determine whether the actual treatment agrees with the therapy plan.

20. A method for loading a plurality of radioactive sources into an insertion device in accordance with a plan, the method comprising:
reading data that describes the plan, the plan data defining (1) a number of radioactive sources to be loaded into the insertion device and (2) a radiation pattern for the plan;
loading a plurality of radioactive sources into the insertion device;
optically sensing the loading of the radioactive sources into the insertion device;

detecting a radiation pattern emitted by the loaded insertion device;

determining from the optically sensing step a quantity of radioactive sources within the insertion device;

comparing the determined radioactive source quantity and the detected radiation pattern with the plan data to thereby determine whether the loaded insertion device is in accordance with the plan.

21. The method of claim 20 wherein the plan data further defines a number of spacers to be loaded into the insertion device, the method further comprising:

loading at least one spacer into the insertion device, the at least one spacer interspersed within the insertion device between radioactive sources;

optically sensing the loading of the at least one spacer; and determining from the spacer optically sensing step a quantity of spacers within the insertion device; and wherein the comparing step further comprises comparing the determined spacer quantity with the plan data to thereby determine whether the loaded insertion device is in accordance with the plan.

22. The method of claim 21 wherein the loading of the radioactive sources and the at least one spacer is performed automatically based on the plan data.

23. The method of claim 22 wherein the plan corresponds to a plurality of insertion devices being loaded with radioactive sources and spacers, the method further comprising performing the aforementioned steps for each of the insertion devices.

24. The method of claim 22 further comprising notifying a user via an alarm if the comparing step determines that the loaded insertion device is not in agreement with the plan.

25. The method of claim 22 wherein the step of optically sensing loading of the radioactive sources comprises optically sensing loading of the radioactive sources via a plurality of redundant optical sensors.

26. The method of claim 22 wherein the step of detecting the radiation pattern comprises detecting the radiation pattern via a plurality of redundant radiation sensors.

27. The method of claim 22 further comprising performing the aforementioned steps in preparation for a prostate brachytherapy procedure.

28. The method of claim 22 further comprising performing the aforementioned steps in preparation for a tissue ablation procedure.

29. A loading system for preparation for therapy of a treatment region of the body of a patient in accordance with a therapy plan, the system comprising:

a first container for holding a plurality of seeds for treatment of the patient, each seed held by the first container emitting a first amount of radiation;

a second container for holding a plurality of seeds for treatment of the patient, each seed held by the second container emitting a second amount of radiation;

a third container for holding a plurality of spacers;

an insertion device for holding selected ones of the first container seeds, second container seeds, and spacers, the insertion device for insertion into the treatment region of the patient to deliver therapy thereto;

a processor configured to read data describing the plan, the plan data defining how selected ones of the first container seeds, second container seeds, and spacers to be loaded into the insertion device;

an auto-loader for automatically loading selected ones of the first container seeds, second container seeds, and spacers into the insertion device in accordance with the plan data;

a plurality of passageways leading from the auto-loader to the insertion device, each passageway corresponding with a different one of the containers, wherein the auto-loader is configured to automatically load selected ones of the first container seeds, second container seeds, and spacers into the insertion device through the passageways; and a plurality of automated sensors positioned to automatically monitor passage of first container seeds, second container seeds, and spacers into the insertion device, thereby generating sensor output data indicative thereof, wherein the plurality of automated sensors comprise (1) at least one automated sensor positioned to monitor passage of a first container seed through the passageway corresponding to the first container, (2) at least one automated sensor positioned to monitor passage of a second container seed through the passageway corresponding to the second container, (3) at least one automated sensor positioned to monitor passage of a spacer through the passageway corresponding to the third container, and (4) at least one automated sensor positioned to monitor passage into the insertion device of all of the selected ones of the first container seeds, second container seeds, and spacers; and wherein the processor is in communication with the automated sensors and is further configured to (1) process the sensor output to determine a quantity of the selected ones of the first container seeds, second container seeds, and spacers that have been loaded into the insertion device, and (2) compare the determined quantity with the plan data to thereby determine whether the loaded insertion device complies with the plan.

30. The system of claim 29 wherein the automated sensors comprise optical sensors.

31. The system of claim 30 wherein the plurality of automated optical sensors further comprise:

a plurality of redundant automated optical sensors positioned to monitor passage of a first container seed through the passageway corresponding to the first container;

a plurality of redundant automated optical sensors positioned to monitor passage of a second container seed through the passageway corresponding to the second container;

a plurality of redundant automated optical sensors positioned to monitor passage of a spacer through the passageway corresponding to the third container; and a plurality of redundant automated optical sensors positioned to monitor passage into the insertion device of all of the selected ones of the first container seeds, second container seeds, and spacers.

32. The system of claim 30 wherein the seeds comprise radioactive sources, the first container radioactive sources emitting a first level of radioactivity, the second container radioactive source emitting a second level of radioactivity, wherein the plan data further defines a level of radiation activity and a radiation contour for the plan, the system further comprising:

at least one radiation sensor positioned to detect a level of radiation activity and a radiation contour collectively emitted by the selected ones of the first container radioactive sources, second container radioactive sources, and spacers that have been loaded into the insertion device; and wherein the processor is in communication with the at least one radiation sensor and is further configured to compare the detected radiation activity level and the detected radiation contour with the plan data to thereby determine whether the loaded insertion device complies with the plan.

33. The system of claim 32 wherein the at least one radiation sensor comprises a plurality of redundant radiation sensors.

* * * * *